(12) United States Patent
Liang et al.

(10) Patent No.: US 11,530,195 B1
(45) Date of Patent: Dec. 20, 2022

(54) PROTACS TARGETING CORONAVIRUS 3CL PROTEASE AND PREPARATION METHOD AND APPLICATION THEREOF

(71) Applicant: SHAANXI PANLONG PHARMACEUTICAL CO., LTD., Xi'an (CN)

(72) Inventors: Chengyuan Liang, Xi'an (CN); Liang Xin, Xi'an (CN); Lei Tian, Xi'an (CN); Juan Xia, Xi'an (CN); Nan Qin, Xi'an (CN); Jingyi Li, Xi'an (CN); Taotao Qiang, Xi'an (CN); Han Li, Xi'an (CN); Xuechuan Wang, Xi'an (CN); Xiaolin Xie, Xi'an (CN); Dezhu Zhang, Xi'an (CN); Qingbo Zhao, Xi'an (CN); Zhenfeng Shi, Xi'an (CN); Min Li, Xi'an (CN); Shaojun Zhang, Xi'an (CN); Kangxiong Wu, Xi'an (CN); Catherine J Lee, Atlanta, GA (US); Maggie Lewis, North Decatur, GA (US); Zhao Ma, Xi'an (CN); Xuhua Zhou, Xi'an (CN)

(73) Assignee: SHAANXI PANLONG PHARMACEUTICAL CO., LTD., Shaanxi (CN)

(*) Notice: Subject to any disclaimer, the term of this patent is extended or adjusted under 35 U.S.C. 154(b) by 0 days.

(21) Appl. No.: 17/749,517

(22) Filed: May 20, 2022

(30) Foreign Application Priority Data

Mar. 31, 2022 (CN) .......................... 202210335448.3

(51) Int. Cl.
*C07D 401/14* (2006.01)
(52) U.S. Cl.
CPC .................. *C07D 401/14* (2013.01)
(58) Field of Classification Search
CPC .................................................. C07D 401/14
See application file for complete search history.

*Primary Examiner* — Brian E McDowell

(57) ABSTRACT

A compound of formula I or formula II, a pharmaceutically acceptable salt, or a tautomer thereof is disclosed.

formula I

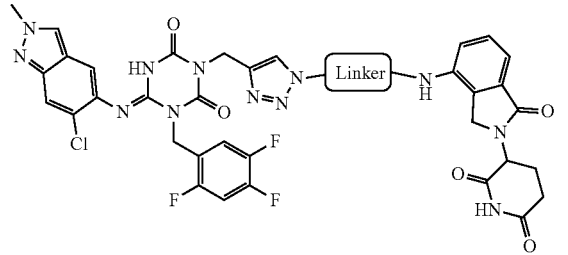

formula II

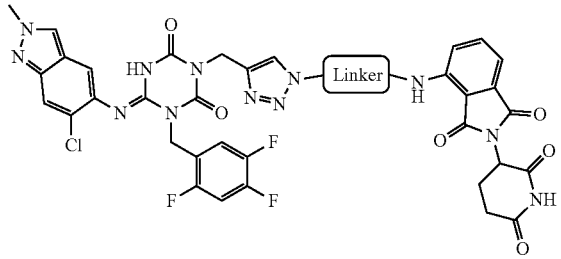

The Linker is

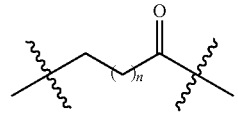

or

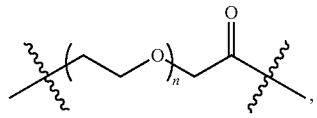

and n is 1-6.

5 Claims, No Drawings

PROTACS TARGETING CORONAVIRUS 3CL PROTEASE AND PREPARATION METHOD AND APPLICATION THEREOF

The present application claims priority to Chinese Patent Application No. 202210335448.3, filed on Mar. 31, 2022, which is incorporated by reference for all purposes as if fully set forth herein.

TECHNICAL FIELD

The present invention relates to the field of medicinal chemistry, and specifically relates to PROTACs targeting coronavirus 3CL protease and a preparation method and application thereof.

BACKGROUND TECHNIQUE

COVID-19 (novel coronavirus SARS-CoV-2) is highly contagious and highly pathogenic, and its mutant strains Delta and Omicron have stronger transmission ability. The endless mutant strains make the global epidemic situation more complicated. The novel coronavirus has posed a serious threat to human health, social stability and economic development.

$3CL^{pro}$ (3C-like protease, also known as major protease $M^{pro}$), as an important non-structural protein in coronaviruses, has a cleavage site specificity similar to the 3C protease of microRNA virus, and plays an important role in the replication and transcription of progeny viruses. to an extremely crucial role. $3CL^{pro}$ is a cysteine protease of about 33 kDa composed of 306 amino acids (much smaller than the S protein), which can specifically recognize 11 cleavage sites of non-structural proteins NSP4-NSP16 and cleaves, thereby releasing other non-structural proteins of the coronavirus. Inhibiting $3CL^{pro}$ can effectively block the process of RNA replication and transcription, thereby blocking the proliferation of the virus. Therefore, $3CL^{pro}$ is considered to be one of the most attractive targets for the development of coronavirus-targeted drugs.

Proteolytic targeting chimeric molecules (PROTACs) are one of the most disruptive technologies in drug development in recent years. Proteolytic targeted chimera (PROTAC) is a technique for chemically degrading proteins. It can bind the target protein and E3 ubiquitin ligase at the same time, make the target protein close to E3 ubiquitin ligase, ubiquitinate the target protein, and then degrade the target protein through the degradation of the ubiquitin-proteasome system (UPS). It is worth mentioning that, regardless of the function of the target protein, it can be degraded by PROTAC technology.

SUMMARY OF THE INVENTION

In one embodiment, the present application discloses a compound of formula I or formula II, a pharmaceutically acceptable salt, or a tautomer thereof.

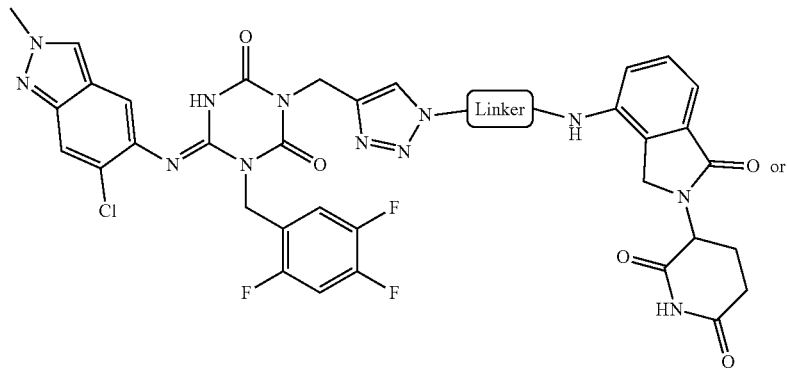

formula I

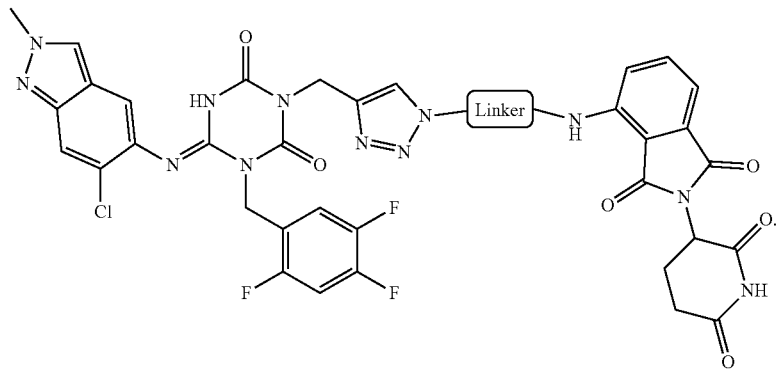

formula II

The Linker is
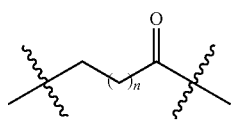 or 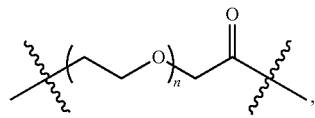
and n is 1-6.
In another embodiment, the compound is selected from the group consisting of
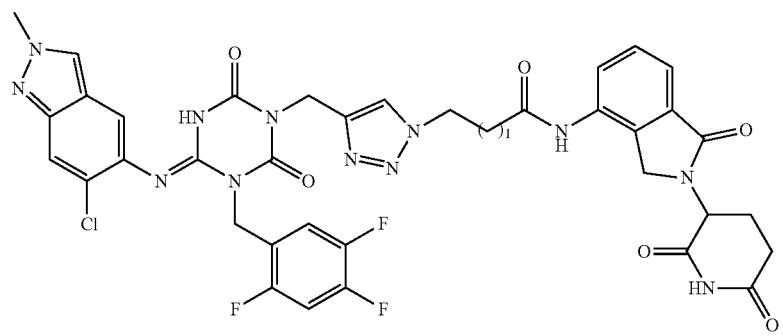
1
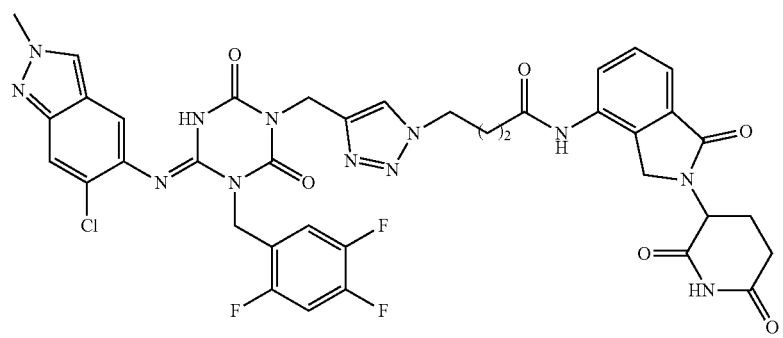
2
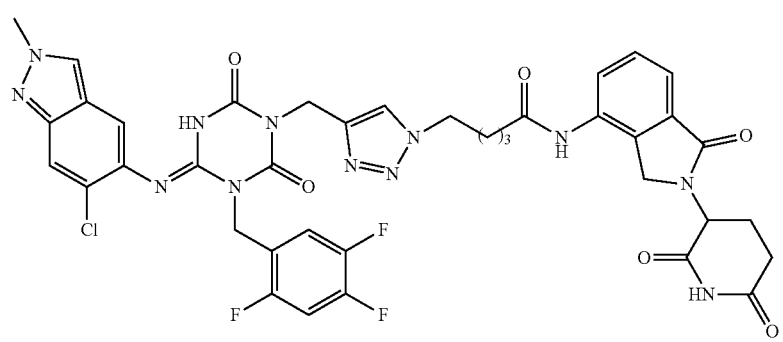
3
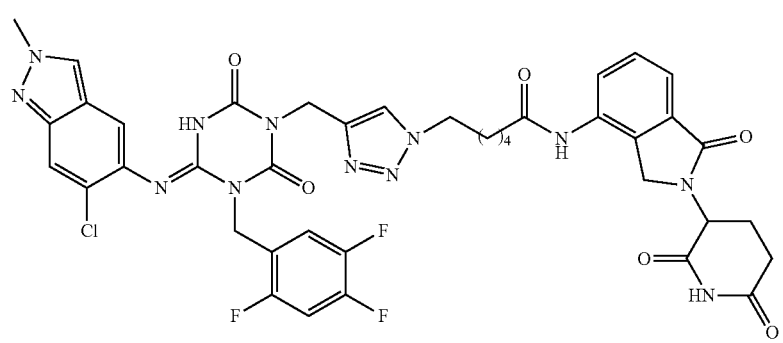
4

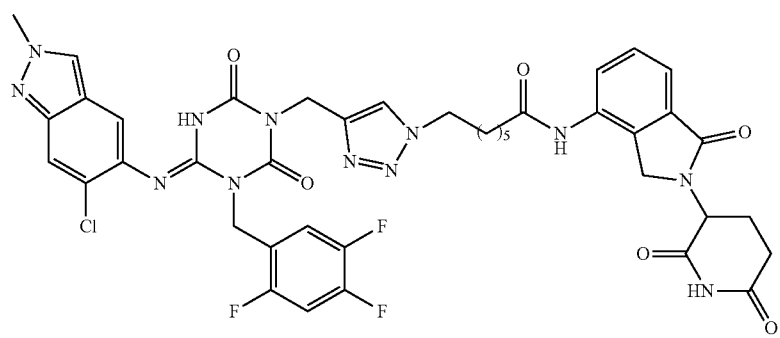
5
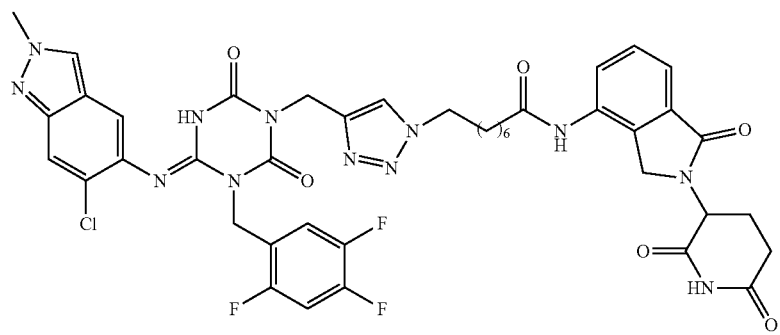
6
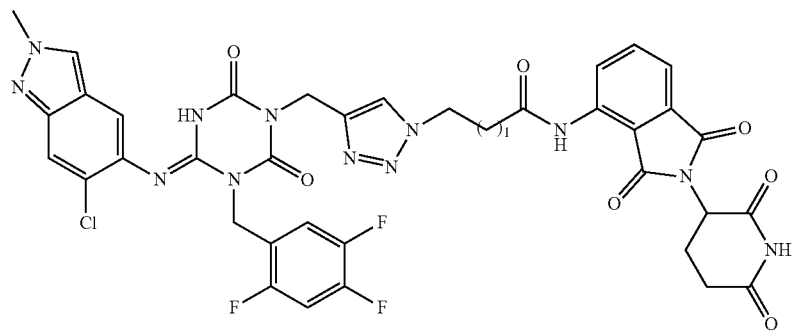
7
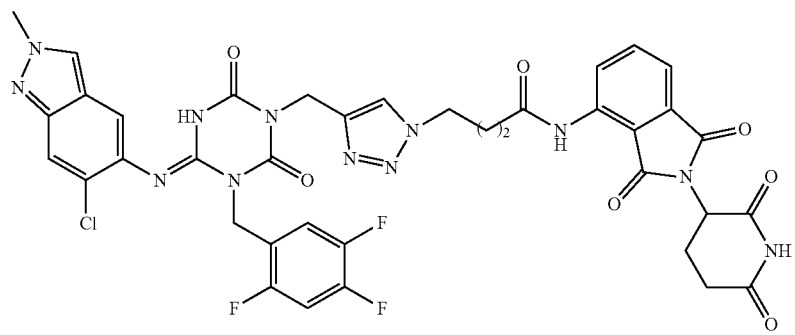
8

-continued
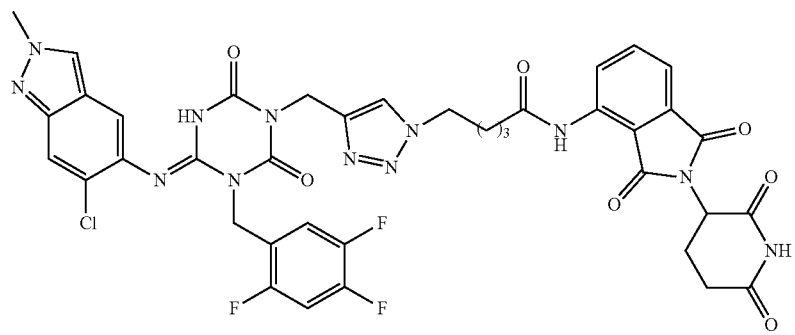
9
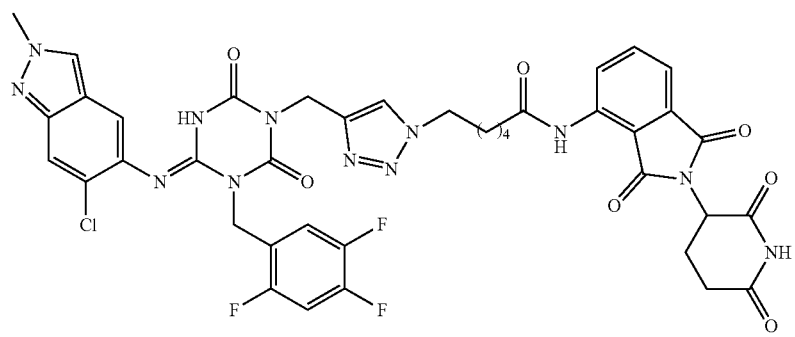
10
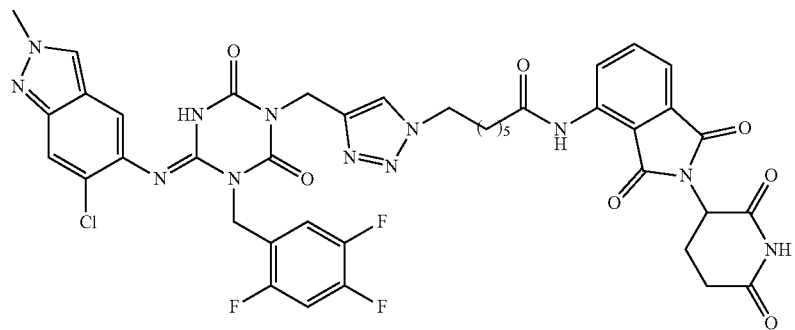
11
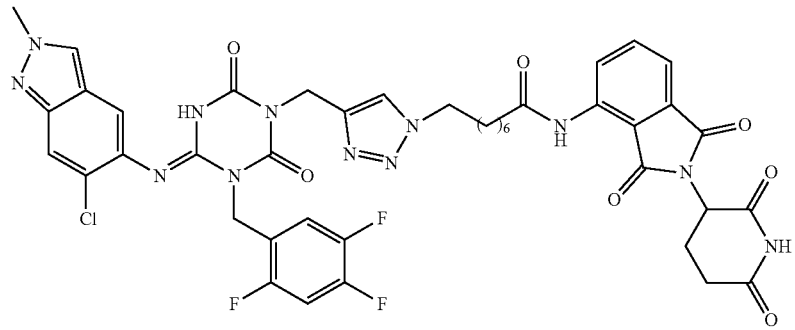
12

13
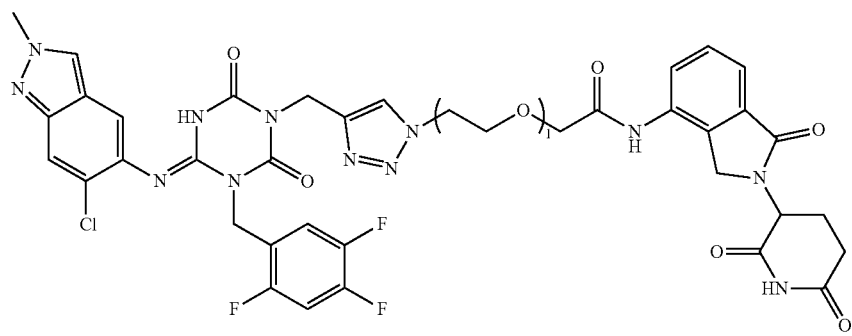
14
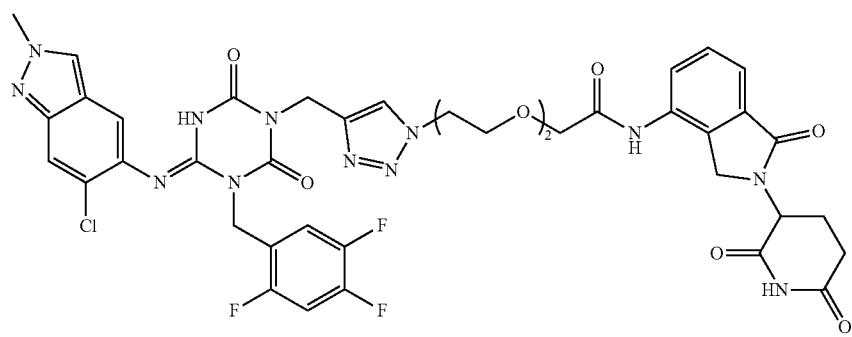
15
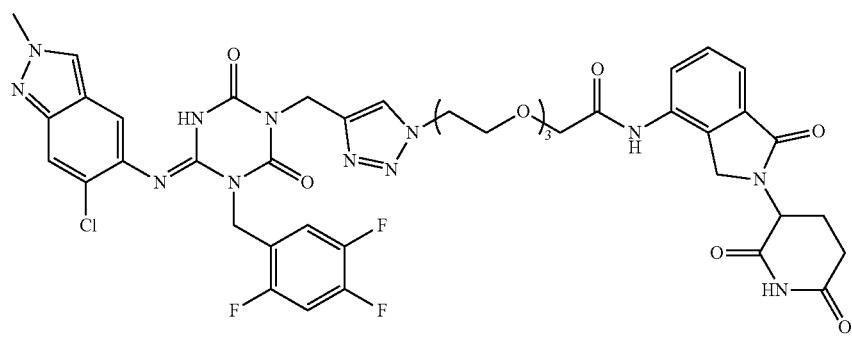
16
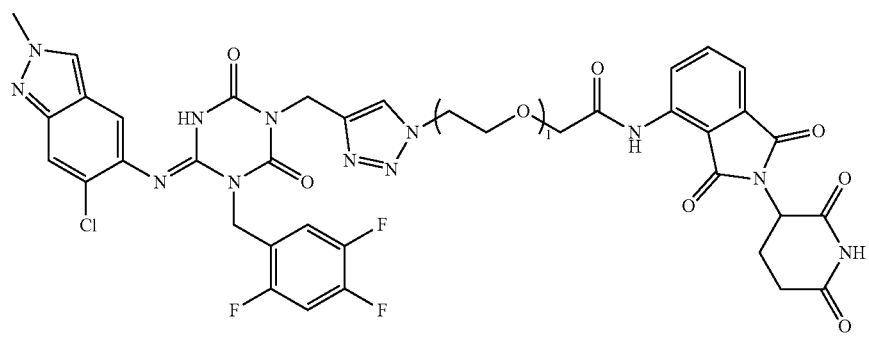

-continued

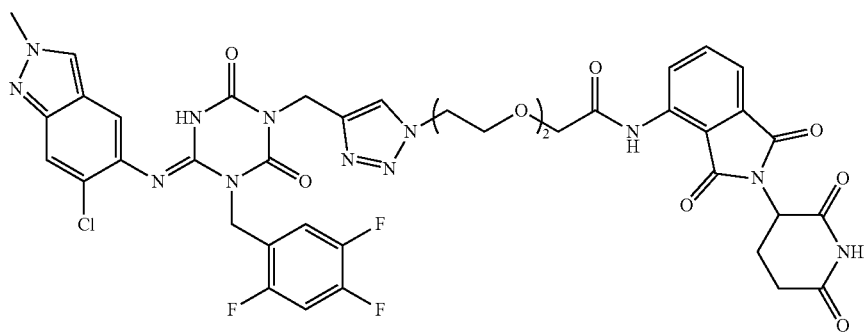

17

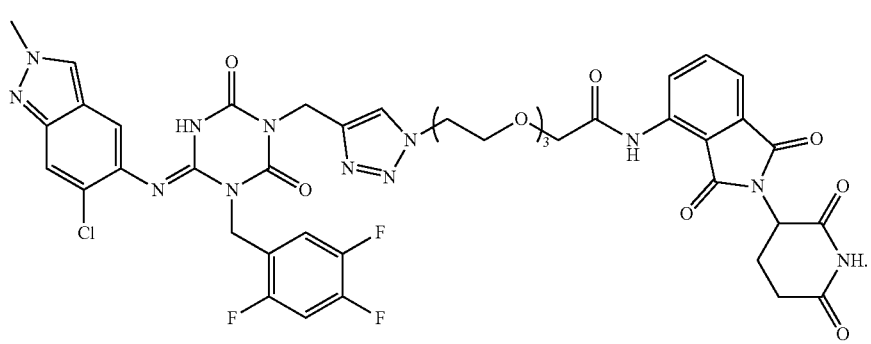

18

In another embodiment, the pharmaceutically acceptable salt includes one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid, and aspartic acid.

In another embodiment, the present application discloses an anti-coronavirus pharmaceutical preparation including the compound of present application.

In another embodiment, in the anti-coronavirus pharmaceutical preparation, the coronavirus is novel coronavirus SARS-CoV-2.

Compared with the prior art, the present invention has the following beneficial effects:

The 3CL$^{pro}$ inhibitory activity test results show that the compounds synthesized in the present invention have strong inhibitory effect on 3CL$^{pro}$, and the IC$_{50}$ values of compounds 3, 4, 8, 9, 10, 14 and 17 are below 100 nM. 3CL$^{Pro}$ degradation activity experimental results show that the compounds synthesized in the present invention all have degrading activity to 3CL$^{pro}$, and the DC$_{50}$ values of compounds 2, 3, 4, 5, 8, 9, 10, 13, 14, 15, 16 and 17 for 3CL$^{pro}$ are all below 100 nM. The compounds provided by the present invention overcome the defects of the existing coronavirus 3CL protease inhibitors, such as single structure type, limited pharmacodynamic pathway (inhibitory effect only).

The invention provides a preparation method of PROTACs targeting coronavirus 3CL protease. The method uses various purchasable low-cost synthetic building blocks as raw materials, and obtains the target product with a higher yield through common chemical reactions.

All reactions avoid the use of high temperature, high pressure and highly toxic reagents, and can be carried out under relatively mild conditions, with low requirements for reaction equipment and low environmental pollution; at the same time, the atom economy is high and suitable for industrial production.

DETAILED DESCRIPTION

In order to make those skilled in the art better understand the solutions of the present invention, the technical solutions in the embodiments of the present invention will be clearly and completely described below with reference to the accompanying drawings in the embodiments of the present invention. Obviously, the described embodiments are only Embodiments are part of the present invention, but not all of the embodiments. Based on the embodiments of the present invention, all other embodiments obtained by persons of ordinary skill in the art without creative efforts shall fall within the protection scope of the present invention.

It is to be understood that the data so used may be interchanged under appropriate circumstances such that the embodiments of the invention described herein can be practiced in sequences other than those illustrated or described herein. Furthermore, the terms "comprising" and "having," and any variations thereof, are intended to cover non-exclusive inclusion, for example, a process, method, system, product or device comprising a series of steps or units is not necessarily limited to those expressly listed Rather, those steps or units may include other steps or units not expressly listed or inherent to these processes, methods, products or devices.

The present application discloses a compound of formula I or formula II, a pharmaceutically acceptable salt, or a tautomer thereof:

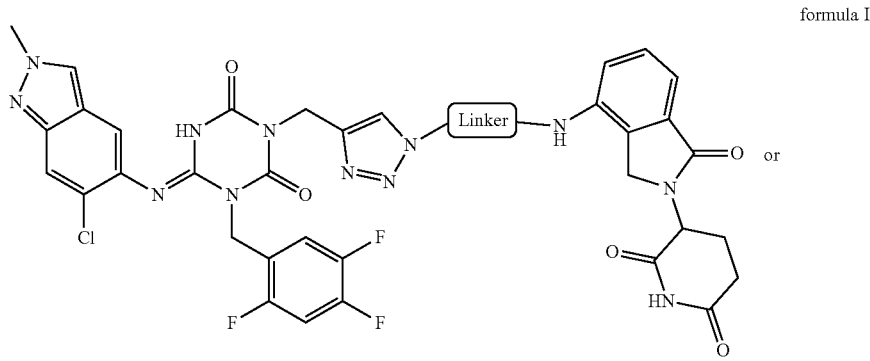

formula I

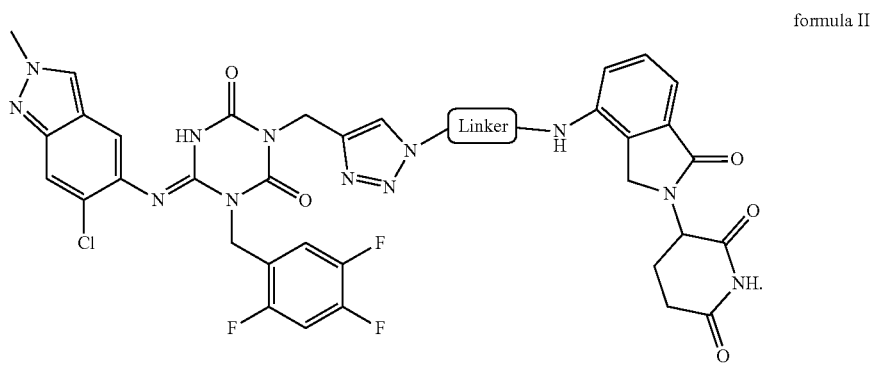

formula II

The Linker is

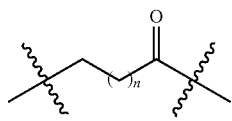

or

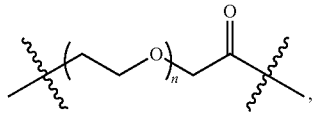

and n is 1-6.

The pharmaceutically acceptable salt includes a salt selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid, and aspartic acid.

The compounds of the present application can be synthesized by a method that includes the following operation steps:

(1) Using 3-tert-butyl-6-(ethylthio)-1,3,5-triazine-2,4(1H, 3H)-dione as raw material, 2,4,5-trifluoro Benzyl bromide is alkylated to obtain compound (a1); 6-chloro-2-methyl-2H-indazole unit is introduced into the 6-position of the triazine nucleus to obtain compound (2a); the 3-position tert-butyl group of the triazine nucleus of compound (a2) is removed in an acidic solvent to obtain compound (a3); a 3-propynyl group is introduced into the 3-position of the triazine nucleus of compound (a3) to finally obtain compound (a4). The reaction scheme is follows.

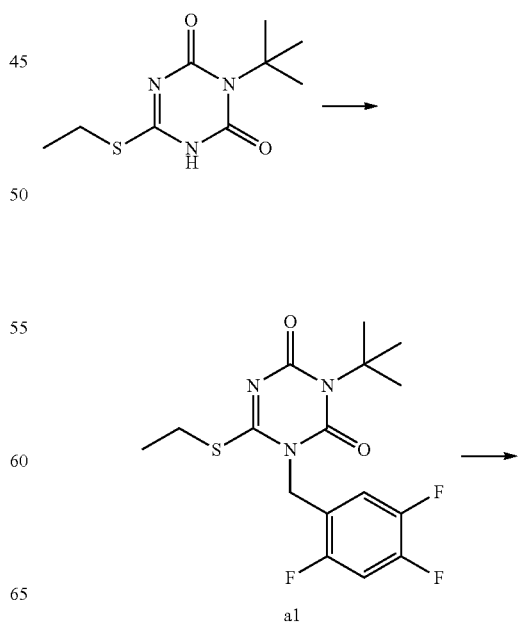

-continued

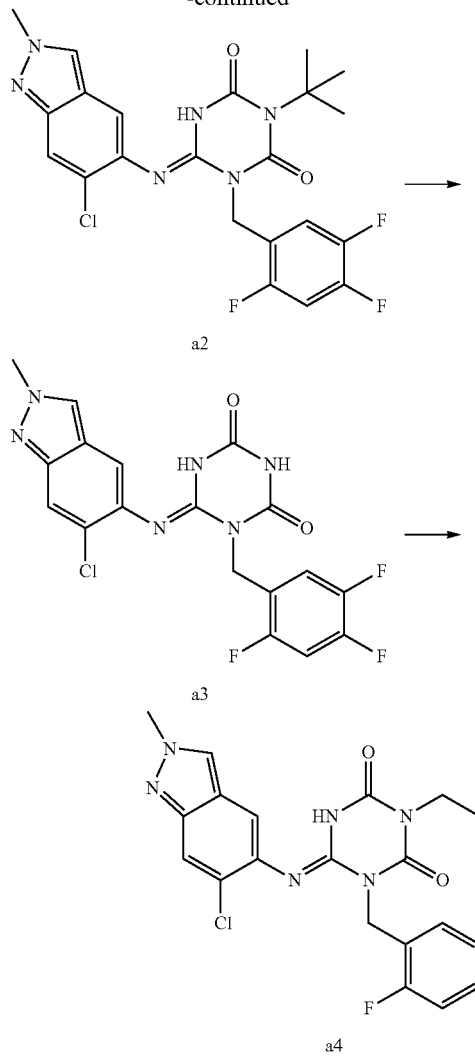

The solvent used in the synthesis process of compound (a1) is acetonitrile. A molar ratio of 3-tert-butyl-6-(ethylthio)-1,3,5-triazine-2,4(1H,3H)-dione and 2,4,5-trifluorobenzyl bromide is 1:1.1. The reaction is carried out with potassium carbonate and under heating and refluxing conditions. In the synthesis process of compound (a2), a molar ratio of the compound (a1) and 6-chloro-2-methyl-2H-indazol-5-amine is 1:1.3, the reaction temperature is 0° C., the solvent used is tetrahydrofuran, and the catalyst used is lithium bistrimethylsilyl amide (LiHMDS). In the synthesis process of compound (a3), the acid solvent used is trifluoroacetic acid (TFA). In the synthesis of compound (a4), a molar ratio of the compound (a3) to 3-bromopropyne is 1:1.2, the solvent used is N,N-dimethylformamide (DMF), and the reaction temperature is 60° C.

(2) Using lenalidomide as raw material, acid-amine condensation reaction with bromoalkanoic acids of different lengths yields the corresponding compounds (b1)-(b6). The compounds (b1)-(b6) react with sodium azide under the catalysis of potassium iodide to obtain the corresponding compounds (c1)-(c6).

Alternatively, using pomalidomide as a raw material, acid-amine condensation reaction with bromoalkanoic acids of different lengths is carried out to obtain the corresponding compounds (b7)-(b12). The compounds (b7)-(b12) react with sodium azide under the catalysis of potassium iodide to obtain the corresponding compounds (c7)-(c12). The reaction scheme is follows.

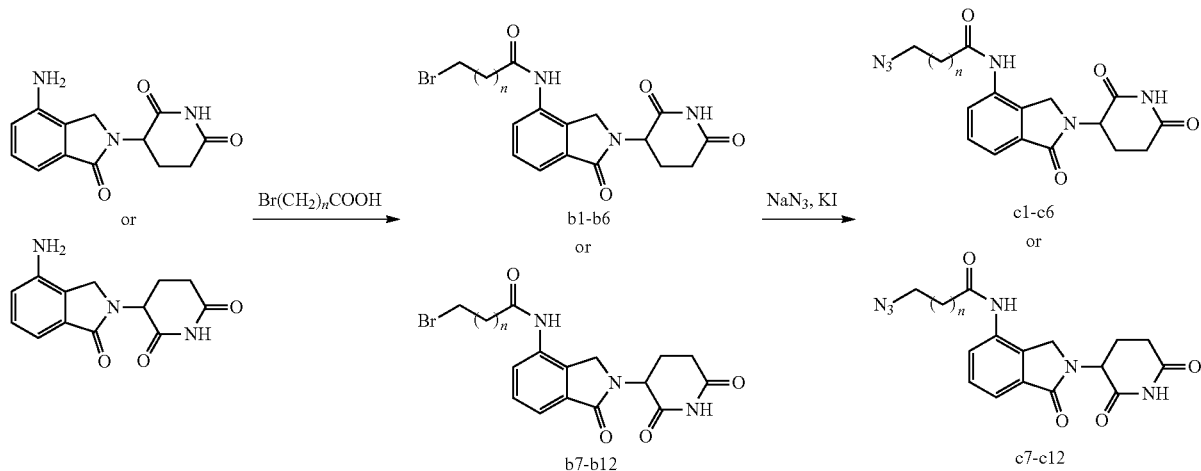

Alternatively, lenalidomide is used as a raw material, and an acid-amine condensation reaction is carried out with an azide-polyethylene glycol-acetic acid compound to obtain the corresponding compounds (d1)-(d3).

Alternatively, pomalidomide is used as raw material, and an acid-amine condensation reaction with an azide-polyethylene glycol-acetic acid compound is carried out to obtain corresponding compounds (d4)-(d6).

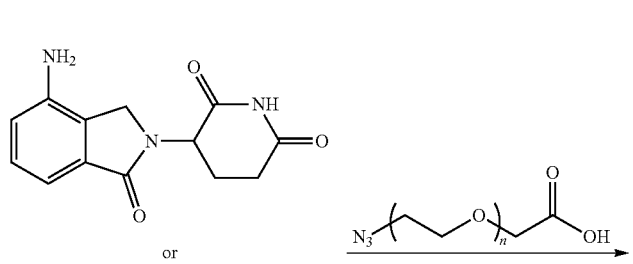

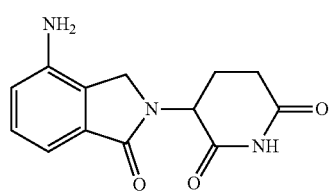

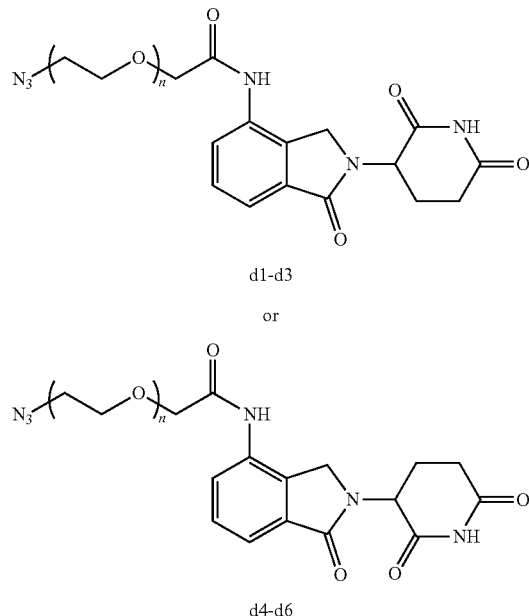

(3) Compound (a4) reacts with compounds (c1)-(c6) or (d1)-(d3) to synthesize compounds of formula I.

Alternatively, compound (a4) reacts with (c7)-(c12) or (d4)-(d6) to synthesize compounds of formula II

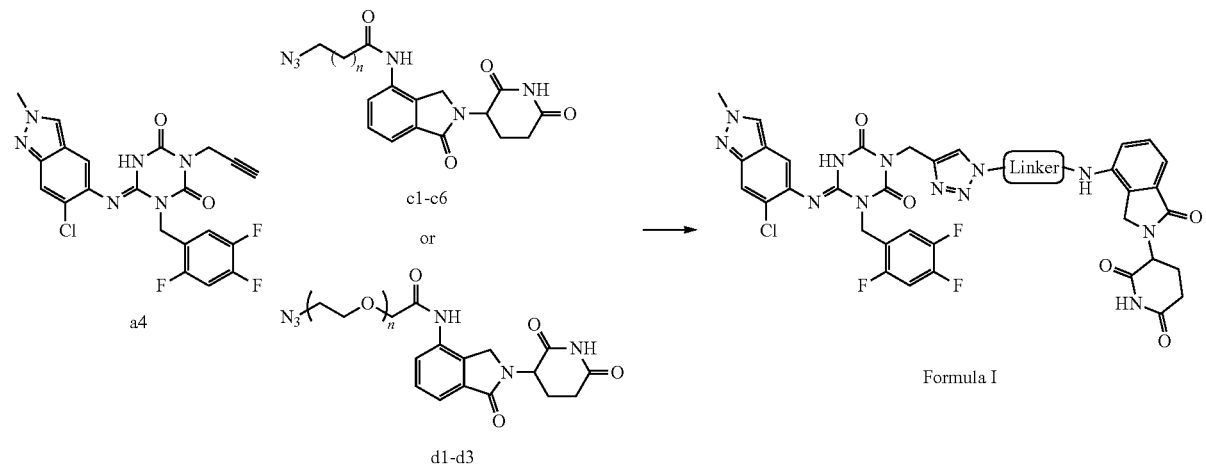

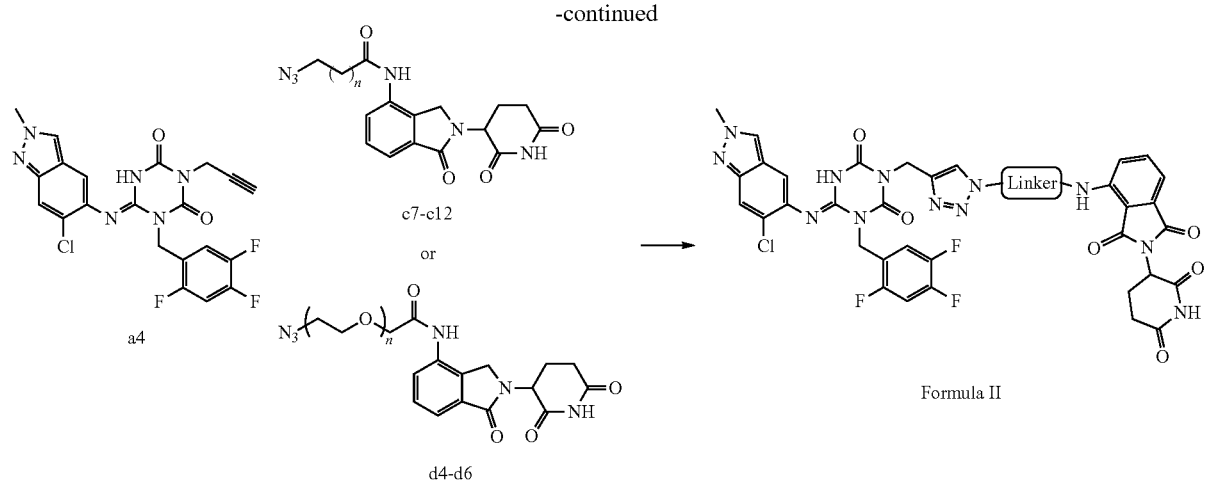

A molar ratio of compound (a4) to compounds (c1)-(c12) or (d1)-(d6) in the reaction is 1:1.2, the solvent used in the reaction is a mixed solvent of tetrahydrofuran and water, and a volume ratio is tetrahydrofuran:water=10:1. The catalyst is copper sulfate pentahydrate and sodium ascorbate. Reaction conditions are 45° C. under argon protection.

Examples of the synthesis of the above compounds are given below.

Example 1

Compound 1: (E)-3-(4-((4-(((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-Dioxypiperidin-3-yl)-1-oxoisoquinolin-4-yl)propanamide (1) Preparation of Compound (a4)

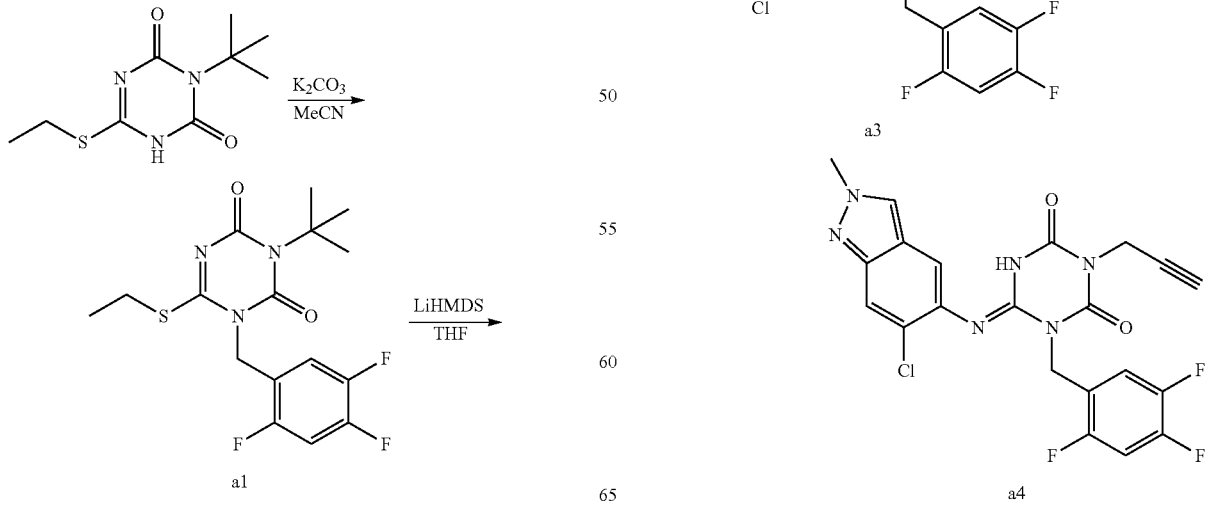

Step 1: Synthesis of Compound (a1)

3-tert-Butyl-6-(ethylthio)-1,3,5-triazine-2,4(1H,3H)-dione (91.72 mg, 0.4 mmol), 2,4,5-triazine fluorobenzyl bromide (99.0 mg, 0.44 mmol) and potassium carbonate (66.3 mg, 0.48 mmol) were placed in a reactor, dissolved in 10 mL of acetonitrile, heated to reflux, stirred for 3 hours, and monitored by TLC. After the reaction was complete, the reaction solution was concentrated under reduced pressure to remove the solvent. The obtained solid residue was washed with saturated aqueous sodium chloride solution, extracted with ethyl acetate. The organic phase was collected, and separated and purified by column chromatography (eluent:n-hexane:ethyl acetate (V:V)=8:2), dried to obtain (a1) 133.3 mg of compound (a1), a yield of 89.25%.

Step 2: Synthesis of Compound (a2)

Compound (a1) (186.7 mg, 0.5 mmol) and 6-chloro-2-methyl-2H-indazol-5-amine (118.1 mg, 0.65 mmol) were placed in a reactor, and dissolved in 5 mL of tetrahydrofuran. A solution of 1 mmol lithium bistrimethylsilylamide (LiHMDS) (0.2 mL, 1 mmol) in tetrahydrofuran was slowly added to the reactor at 0° C., and the reaction was stirred for 3 hours and monitored by TLC. After the reaction was completed, the mixture was cooled to room temperature, and quenched with an aqueous ammonium chloride solution. The reaction solution was concentrated under reduced pressure to remove tetrahydrofuran. The resulting residue was washed with saturated aqueous sodium chloride solution, and extracted with ethyl acetate. The organic phase was collected and separated by column chromatography (eluent: dichloromethane:methanol (V:V)=10; 1), and dried to give 60.7 mg of compound (a2), a yield 24.63%.

Step 3: Synthesis of Compound (a3)

The obtained compound (a2) (246.4 mg, 0.5 mmol) was placed in a reactor, added 3 mL of trifluoroacetic acid (TFA), stirred at room temperature overnight, azeotropically concentrated with toluene to remove the solvent, and dried to obtain 201.0 mg of compound (a3), a yield of 92.03%.

Step 4: Synthesis of Compound (a4)

Compound (a3) (436.8 mg, 1 mmol), 3-bromopropyne (0.1 mL, 1.2 mmol) and potassium carbonate (165.9 mg, 1.2 mmol) were placed in a reactor, dissolved in 10 mL N,N-dimethylmethane, heated and stirred at 60° C. for 5 hours, and monitored by TLC. After the reaction was complete, the reaction solution was washed with saturated aqueous sodium chloride solution, and extracted with ethyl acetate. The organic phase was collected, separated and purified by column chromatography (eluent: n-hexane:ethyl acetate (V:V)=6:4), and dried to obtain 312.0 mg of compound (a4), a yield of 65.71%.

(2) Preparation of Compound (c1)

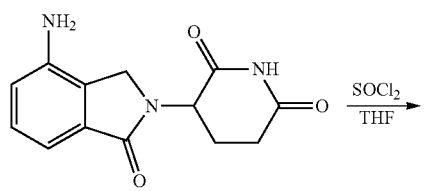

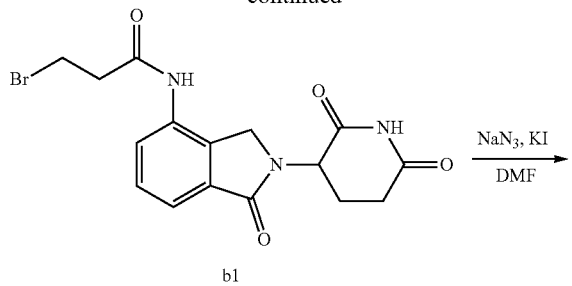

b1

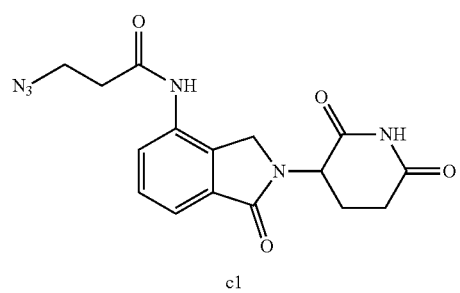

c1

Step 1: Synthesis of Compound (b1)

3-Bromopropionic acid (305.9 mg, 2 mmol) was dissolved in 5 mL of thionyl chloride, and heated to reflux for 2 hours. After the reaction was completed, the reaction mixture was concentrated under reduced pressure to remove the solvent. Then lenalidomide (1 mmol, 259.3 mg) in 10 mL of tetrahydrofuran was added, and the reaction was heated under reflux for 5 hours, monitored by TLC. After the reaction was completed, the reaction mixture was cooled to room temperature, added 2 mL of methanol, and stirred for 1 hour. The solvent was removed by concentration under reduced, and the residue was purified by column chromatography (eluent: dichloromethane:methanol (V:V)=20:1) to obtain 362.1 mg of compound (b1), a yield of 91.85%.

Step 2: Synthesis of Compound c1

Compound b1 (197.1 mg, 0.5 mmol), sodium azide (97.5 mg, 1.5 mmol) and potassium iodide (8.3 mg, 0.05 mmol) were placed in a reactor, dissolved in 10 mL of N,N-dimethylformamide, heated and stirred at 70° C. for 5 hours, and monitored by TLC. After the reaction was complete, the reaction mixture was washed with saturated aqueous sodium chloride solution, and extracted with ethyl acetate. The organic phase was collected and dried to obtain 151.6 mg of compound (c1), a yield of 85.16%.

(4) Preparation of Compound 1

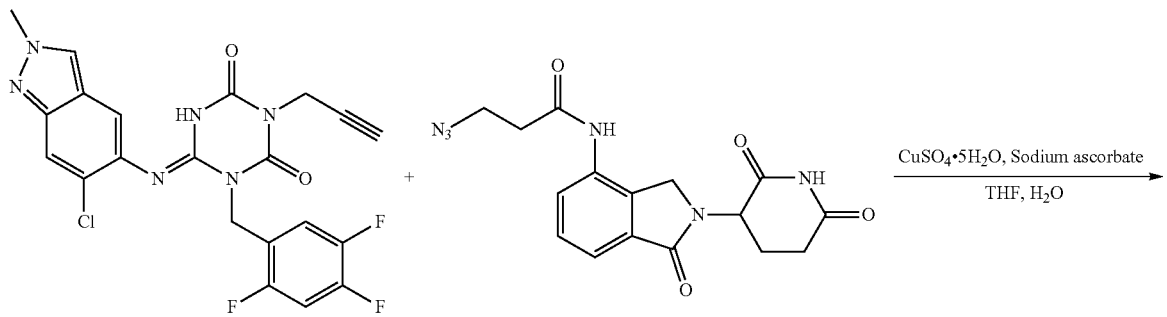

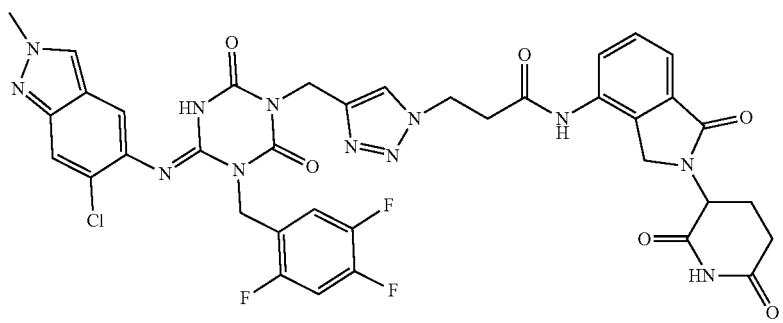

Compound (a4) (142.4 mg, 0.3 mmol), compound (c1) (128.3 mg, 0.36 mmol) and copper sulfate pentahydrate (30.0 mg, 0.12 mmol), sodium ascorbate (23.8 mg, 0.12 mmol) were placed in a reactor, dissolved in a mixture of 10 mL tetrahydrofuran and 1 mL water, heated and stirred at 45° C. overnight under argon, and monitored by TLC. After the reaction was complete, the reaction mixture was concentrated under reduced pressure to remove the solvent, separated and purified by column chromatography (eluent: dichloromethane:methanol (V:V)=15:1), and dried to obtain 95.7 mg of compound 1, a yield of 38.41%.

$^1$H NMR (400 MHz, DMSO) δ 11.10 (s, 1H), 9.79 (s, 1H), 9.33 (s, 1H), 8.32 (s, 1H), 7.85 (d, J=7.1 Hz, 1H), 7.75 (s, 1H), 7.62-7.50 (m, 2H), 7.44-7.37 (m, 2H), 7.30 (s, 1H), 7.28-7.21 (m, 1H), 5.22 (s, 2H), 5.12 (dd, J=13.3, 4.8 Hz, 1H), 5.03 (s, 2H), 4.57 (t, J=6.8 Hz, 2H), 4.45-4.23 (m, 2H), 4.12 (3H, s), 3.04-2.86 (m, 1H), 2.70 (d, J=17.3 Hz, 1H), 2.33-2.12 (m, 2H), 1.95-1.78 (m, 2H).

$^{13}$C NMR (101 MHz, DMSO) δ 173.34, 171.42, 171.25, 168.38, 155.61, 155.17, 150.54, 150.41, 148.55, 146.65, 146.31, 145.74, 143.88, 134.34, 133.12, 132.13, 129.10, 129.02, 127.24, 125.89, 125.82, 120.70, 120.41, 119.44, 118.11, 116.74, 116.36, 106.12, 52.08, 46.94, 40.28, 40.13, 38.05, 36.15, 35.60, 31.65, 28.68.

Example 2

Compound 2: (E)-4-(4-((4-((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-dioxopiperidin-3-yl)-1-oxoisoquinolin-4-yl)butanamide

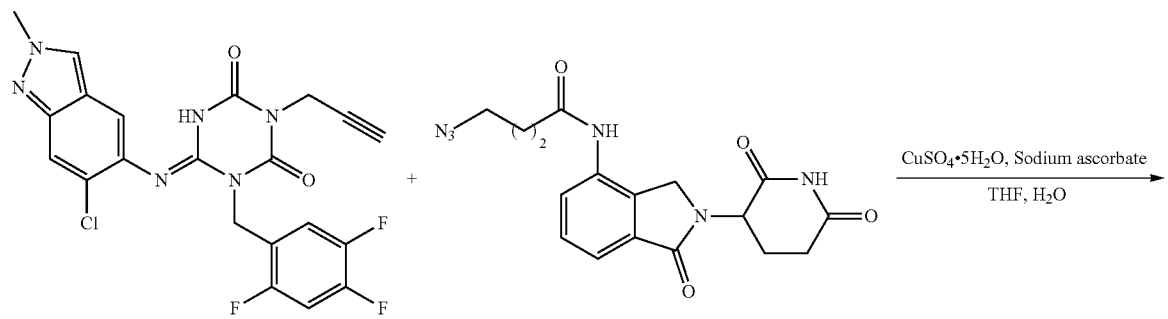

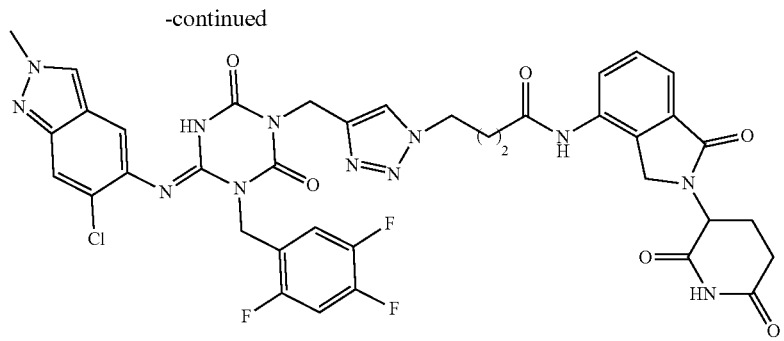

Compound 2 was prepared in the same way as Compound 1 with different starting materials, a yield of 35.23%.

¹H NMR (400 MHz, DMSO) δ 11.12 (s, 1H), 9.77 (s, 1H), 9.32 (s, 1H), 8.29 (s, 1H), 7.88 (d, J=7.1 Hz, 1H), 7.71 (s, 1H), 7.65-7.53 (m, 2H), 7.48-7.40 (m, 2H), 7.35 (s, 1H), 7.32-7.21 (m, 1H), 5.28 (s, 2H), 5.21 (dd, J=13.3, 4.8 Hz, 1H), 5.05 (s, 2H), 4.69 (t, J=6.8 Hz, 2H), 4.43-4.29 (m, 2H), 4.16 (3H, s), 3.02-2.81 (m, 1H), 2.60 (d, J=17.3 Hz, 1H), 2.50-2.38 (m, 3H), 2.09-2.01 (m, 1H), 1.92-1.80 (m, 2H).

¹³C NMR (101 MHz, DMSO) δ 173.35, 171.46, 171.26, 168.39, 155.65, 155.15, 150.56, 150.42, 148.57, 146.69, 146.34, 145.77, 143.89, 134.36, 133.15, 132.16, 129.12, 129.00, 127.23, 125.91, 125.80, 120.71, 120.43, 119.46, 118.10, 116.79, 116.32, 106.11, 52.06, 46.84, 40.21, 40.10, 38.06, 36.12, 35.59, 31.61, 27.58, 24.65.

Example 3

Compound 3: (E)-5-(4-((4-((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-Dioxypiperidin-3-yl)-1-oxoisoquinolin-4-yl)pentanamide Compound 3 was prepared in the same way as Compound 1 with different starting materials, a yield of 30.76%.

¹H NMR (400 MHz, DMSO) δ 11.11 (s, 1H), 9.79 (s, 1H), 9.28 (s, 1H), 8.36 (s, 1H), 7.84 (d, J=7.1 Hz, 1H), 7.75 (s, 1H), 7.63-7.52 (m, 2H), 7.47-7.41 (m, 2H), 7.36 (s, 1H), 7.32-7.22 (m, 1H), 5.24 (s, 2H), 5.20 (dd, J=13.3, 4.8 Hz, 1H), 5.07 (s, 2H), 4.72 (t, J=6.8 Hz, 2H), 4.44-4.30 (m, 2H), 4.18 (3H, s), 3.06-2.88 (m, 1H), 2.61 (d, J=17.3 Hz, 1H), 2.51-2.40 (m, 3H), 2.09-2.01 (m, 1H), 1.82-1.70 (m, 2H), 1.57-1.41 (m, 2H).

¹³C NMR (101 MHz, DMSO) δ 173.45, 171.56, 171.34, 168.43, 155.62, 155.11, 150.53, 150.41, 148.54, 146.67, 146.33, 145.88, 143.81, 134.34, 133.17, 132.19, 129.10, 129.08, 127.22, 125.90, 125.75, 120.72, 120.44, 119.49, 118.12, 116.80, 116.34, 106.12, 52.00, 46.87, 40.22, 40.11, 38.08, 36.04, 35.62, 32.37, 31.65, 27.5 Example 4 Compound 4: (E)-6-(4-((4-((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-Dioxypiperidin-3-yl)-1-oxoisoquinolin-4-yl)hexanamide

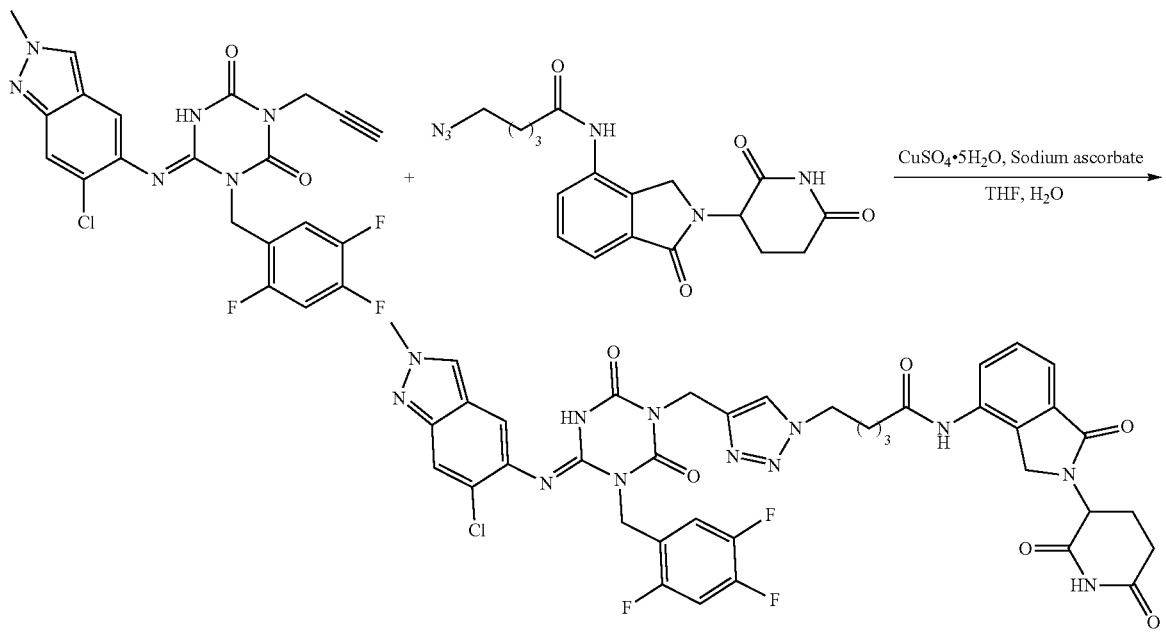

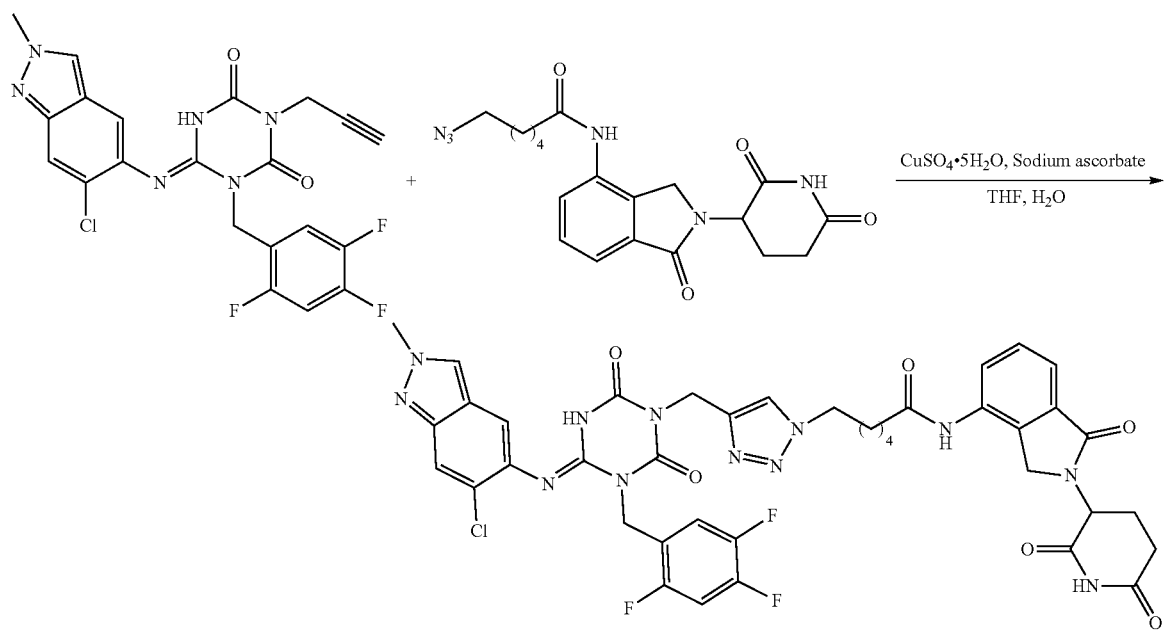

Compound 4 was prepared in the same way as Compound 1 with different starting materials, a yield of 36.55%.

$^1$H NMR (400 MHz, DMSO) δ 11.05 (s, 1H), 9.81 (s, 1H), 9.31 (s, 1H), 8.40 (s, 1H), 7.83 (d, J=7.1 Hz, 1H), 7.73 (s, 1H), 7.65-7.54 (m, 2H), 7.50-7.41 (m, 2H), 7.38 (s, 1H), 7.32-7.25 (m, 1H), 5.26 (s, 2H), 5.18 (dd, J=13.3, 4.8 Hz, 1H), 5.04 (s, 2H), 4.67 (t, J=6.8 Hz, 2H), 4.47-4.31 (m, 2H), 4.15 (3H, s), 3.02-2.88 (m, 1H), 2.64 (d, J=17.3 Hz, 1H), 2.44-2.30 (m, 3H), 2.10-2.02 (m, 1H), 1.92-1.81 (m, 2H), 1.72-1.60 (m, 2H), 1.57-1.41 (m, 2H).

$^{13}$C NMR (101 MHz, DMSO) δ 173.35, 171.68, 171.56, 168.33, 155.58, 155.22, 150.50, 150.43, 148.52, 146.60, 146.38, 145.98, 143.84, 134.26, 133.17, 132.35, 129.12, 129.10, 127.21, 125.93, 125.79, 120.76, 120.54, 119.53, 118.12, 116.70, 116.46, 106.16, 52.00, 46.96, 40.29, 40.06, 38.04, 36.08, 35.61, 32.47, 31.57.1, 23.66

Example 5

Compound 5: (E)-7-(4-((4-(((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-Dioxypiperidin-3-yl)-1-oxoisoquinolin-4-yl)heptamide

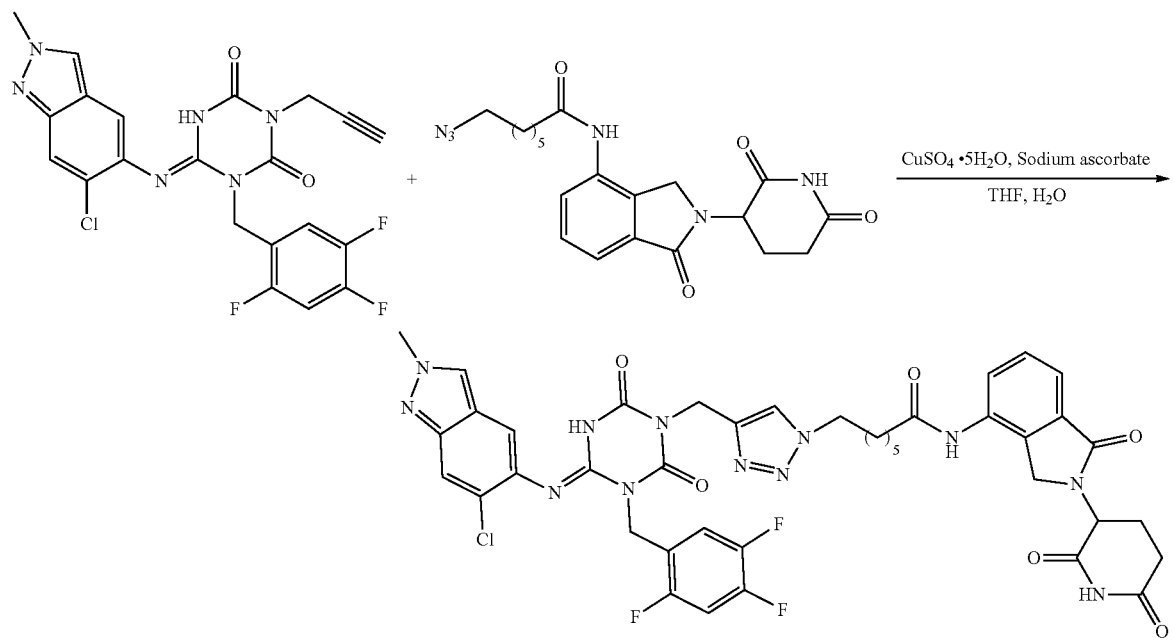

Compound 5 was prepared in the same way as Compound 1 with different starting materials, a yield of 21.18%0.

¹H NMR (400 MHz, DMSO) δ 11.08 (s, 1H), 9.79 (s, 1H), 9.34 (s, 1H), 8.42 (s, 1H), 7.85 (d, J=7.1 Hz, 1H), 7.71 (s, 1H), 7.67-7.54 (m, 2H), 7.49-7.41 (m, 2H), 7.37 (s, 1H), 7.32-7.25 (m, 1H), 5.24 (s, 2H), 5.17 (dd, J=13.3, 4.8 Hz, 1H), 5.02 (s, 2H), 4.63 (t, J=6.8 Hz, 2H), 4.49-4.31 (m, 2H), 4.16 (3H, s), 3.02-2.88 (m, 1H), 2.65 (d, J=17.3 Hz, 1H), 2.42-2.29 (m, 2H), 2.20-2.03 (m, 4H), 1.90-1.79 (m, 2H), 1.70-1.61 (m, 2H), 1.54-1.39 (m, 2H).

¹³C NMR (101 MHz, DMSO) δ 173.39, 171.62, 171.49, 168.36, 155.49, 155.23, 150.51, 150.43, 148.54, 146.62, 146.39, 145.90, 143.81, 134.22, 133.19, 132.29, 129.09, 129.03, 127.26, 125.90, 125.75, 120.72, 120.54, 119.52, 118.11, 116.76, 116.41, 106.14, 52.08, 46.95, 40.30, 40.05, 38.03, 35.59, 31.70, 27.62, 23.35, 23.35.

Example 6

Compound 6: (E)-8-(4-((4-(((6-Chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-dioxopiperidin-3-yl)-1-oxoisoquinolin-4-yl)octamide

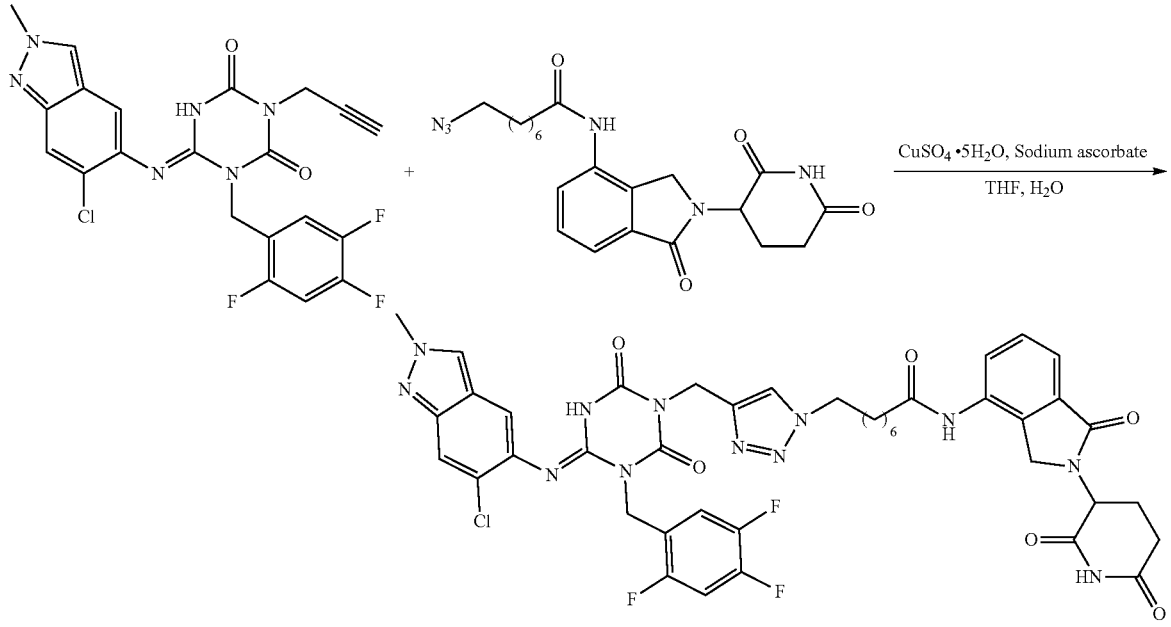

Compound 6 was prepared in the same way as Compound 1 with different starting materials, a yield of 17.83%.

¹H NMR (400 MHz, DMSO) δ 11.12 (s, 1H), 9.76 (s, 1H), 9.33 (s, 1H), 8.41 (s, 1H), 7.88 (d, J=7.1 Hz, 1H), 7.73 (s, 1H), 7.67-7.54 (m, 2H), 7.48-7.42 (m, 2H), 7.36 (s, 1H), 7.31-7.25 (m, 1H), 5.25 (s, 2H), 5.16 (dd, J=13.3, 4.8 Hz, 1H), 5.04 (s, 2H), 4.69 (t, J=6.8 Hz, 2H), 4.45-4.30 (m, 2H), 4.17 (3H, s), 3.08-2.80 (m, 1H), 2.69 (d, J=17.3 Hz, 1H), 2.44-2.29 (m, 2H), 2.24-2.05 (m, 4H), 1.95-1.76 (m, 4H), 1.69-1.58 (m, 2H), 1.49-1.38 (m, 2H).

¹³C NMR (101 MHz, DMSO) δ 173.38, 171.58, 171.46, 168.35, 155.43, 155.24, 150.50, 150.41, 148.53, 146.61, 146.36, 145.91, 143.83, 134.23, 133.18, 132.29, 129.12, 129.02, 127.24, 125.95, 125.78, 120.71, 120.56, 119.52, 118.14, 116.72, 116.44, 106.18, 52.12, 46.98, 40.33, 40.10, 38.08, 35.61, 32.77, 30.15, 27.65, 24.76, 23.42.

Example 7

Compound 7: (E)-3-(4-((4-(((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-dioxopiperidin-3-yl)-1,3-dioxoisoindolin-4-yl)propionamide

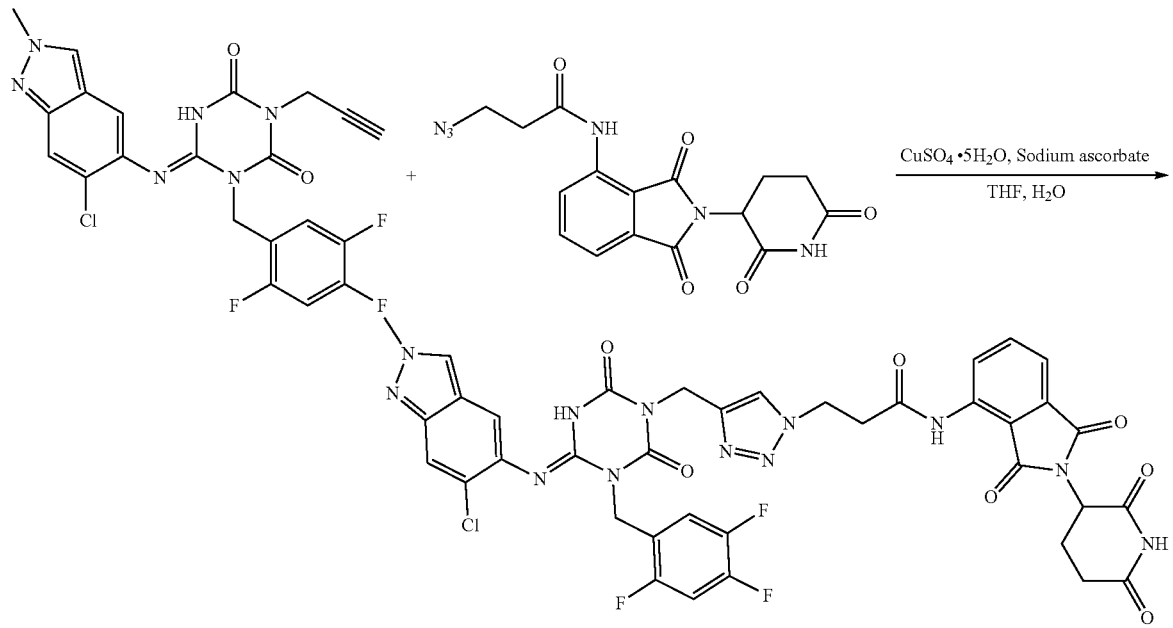

Compound 7 was prepared in the same way as Compound 1 with different starting materials, a yield of 37.54%.

$^1$H NMR (400 MHz, DMSO) δ 11.10 (s, 1H), 9.84 (s, 1H), 9.72 (s, 1H), 8.42 (d, J=8.3 Hz, 1H), 8.33 (s, 1H), 7.79 (t, J=7.8 Hz, 1H), 7.73 (s, 1H), 7.69 (d, J=7.2 Hz, 1H), 7.64-7.53 (m, 2H), 7.42 (s, 1H), 7.32-7.22 (m, 1H), 5.23 (s, 2H), 5.14 (dd, J=12.8, 5.3 Hz, 1H), 5.11 (s, 2H), 4.68 (t, J=6.5 Hz, 2H), 4.21 (s, 3H)), 2.56-2.44 (m, 2H), 2.33-2.21 (m, 2H), 1.95-1.83 (m, 2H). $^{13}$C NMR (101 MHz, DMSO) δ 173.32, 172.23, 170.40, 168.21, 167.23, 155.78, 155.33, 150.89, 150.55, 148.63, 146.66, 146.34, 145.86, 143.82, 136.91, 136.62, 132.32, 131.89, 129.43, 127.32, 126.87, 125.89, 120.82, 120.43, 118.82, 117.78, 116.71, 116.38, 106.21, 48.34, 40.45, 39.89, 37.05, 35.29, 34.22, 32.29, 28.78.

Example 8

Compound 8: (E)-4-(4-((4-(((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-dioxopiperidin-3-yl)-1,3-dioxoisoindolin-4-yl)butanamide

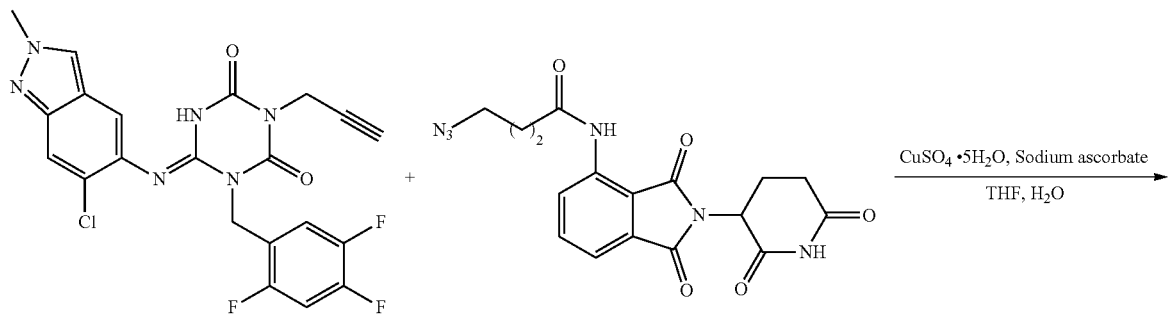

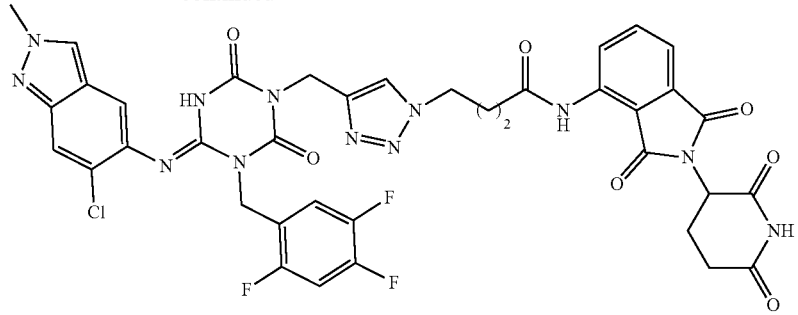

Compound 8 was prepared in the same way as Compound 1 with different starting materials, a yield of 33.77%.

$^1$H NMR (400 MHz, DMSO) δ 11.09 (s, 1H), 9.82 (s, 1H), 9.74 (s, 1H), 8.39 (d, J=8.3 Hz, 1H), 8.35 (s, 1H), 7.86 (t, J=7.8 Hz, 1H), 7.70 (s, 1H), 7.68 (d, J=7.2 Hz, 1H), 7.63-7.53 (m, 2H), 7.33 (s, 1H), 7.29-7.22 (m, 1H), 5.20 (s, 2H), 5.16 (dd, J=12.8, 5.3 Hz, 1H), 5.09 (s, 2H), 4.58 (t, J=6.5 Hz, 2H), 4.16 (s, 3H)), 2.95-2.88 (m, 1H), 2.66-2.54 (m, 2H), 2.43-2.31 (m, 1H), 2.25-2.14 (m, 2H), 1.98-1.84 (m, 2H).

$^{13}$C NMR (101 MHz, DMSO) δ 173.29, 172.19, 170.29, 168.12, 167.21, 155.45, 155.23, 150.55, 150.44, 148.55, 146.62, 146.31, 145.90, 143.85, 136.89, 136.57, 132.34, 131.95, 129.12, 127.31, 126.92, 125.91, 120.75, 120.52, 118.80, 117.69, 116.69, 116.42, 106.17, 49.33, 40.31, 40.12, 38.03, 35.73, 35.20, 32.09, 30.45.24.

Example 9

Compound 9: (E)-5-(4-((4-(((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-dioxopiperidin-3-yl)-1,3-dioxoisoindolin-4-yl)pentanamide

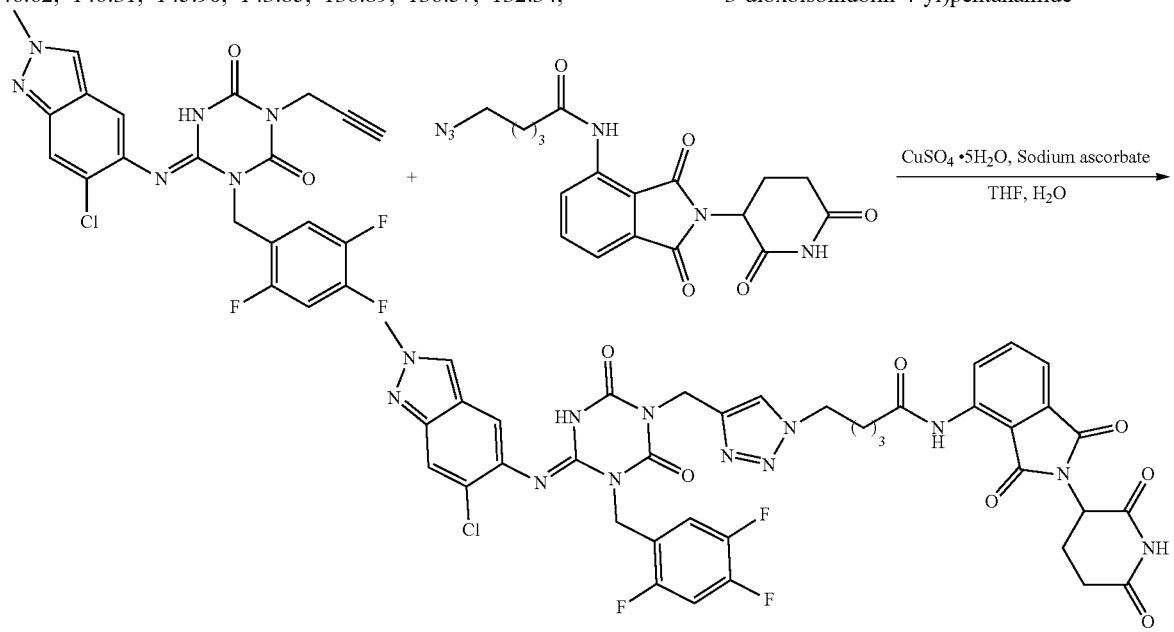

Compound 9 was prepared in the same way as Compound 1 with different starting materials, a yield of 27.64%.

$^1$H NMR (400 MHz, DMSO) δ 11.13 (s, 1H), 9.84 (s, 1H), 9.73 (s, 1H), 8.46 (d, J=8.3 Hz, 1H), 8.42 (s, 1H), 7.86 (t, J=7.8 Hz, 1H), 7.72 (s, 1H), 7.67 (d, J=7.2 Hz, 1H), 7.64-7.53 (m, 2H), 7.36 (s, 1H), 7.30-7.22 (m, 1H), 5.24 (s, 2H), 5.18 (dd, J=12.8, 5.3 Hz, 1H), 5.06 (s, 2H), 4.61 (t, J=6.5 Hz, 2H), 4.14 (s, 3H)), 2.98-2.87 (m, 1H), 2.68-2.52 (m, 4H), 2.13-2.01 (m, 1H), 1.95-1.84 (m, 2H), 1.81-1.64 (m, 2H).

$^{13}$C NMR (101 MHz, DMSO) δ 173.24, 172.17, 170.26, 168.07, 167.14, 155.57, 155.20, 150.51, 150.42, 148.51, 146.64, 146.37, 145.97, 143.81, 136.91, 136.56, 132.35, 131.97, 129.10, 127.36, 126.94, 125.93, 120.76, 120.54, 118.86, 117.65, 116.70, 116.46, 106.16, 49.38, 40.29, 40.06, 38.04, 35.78, 35.17, 32.02, 21.45.

Example 10

Compound 10: (E)-6-(4-((4-(((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-dioxopiperidin-3-yl)-1,3-dioxoisoindolin-4-yl)hexanamide

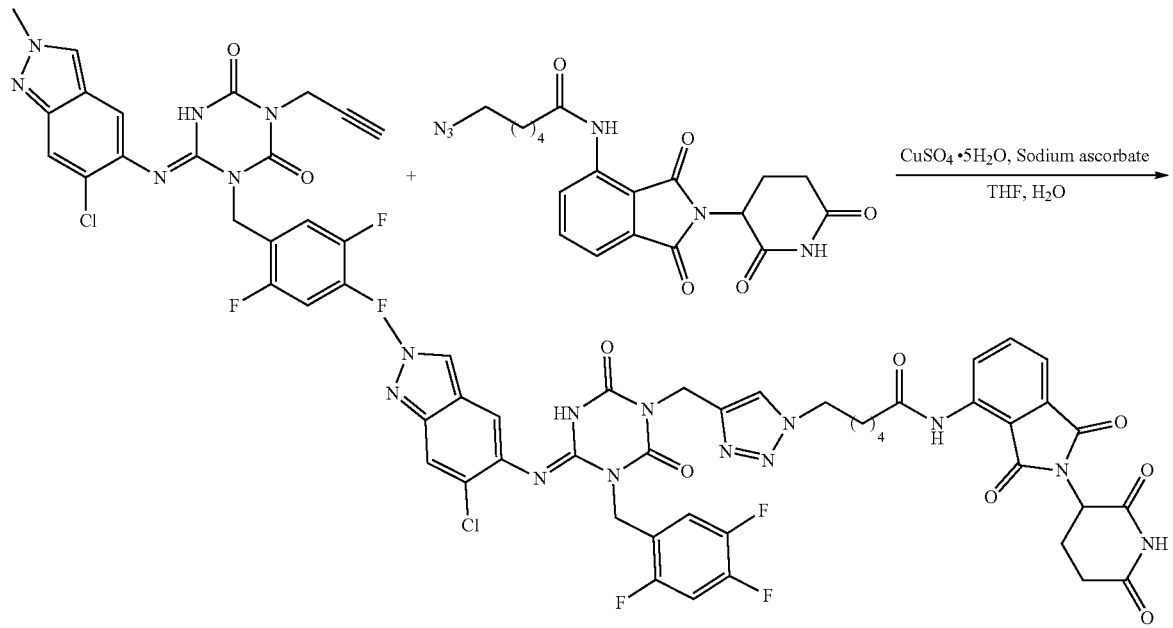

Compound 10 was prepared in the same way as Compound 1 with different starting materials, a yield of 22.19%0.

$^1$H NMR (400 MHz, DMSO) δ 11.14 (s, 1H), 9.90 (s, 1H), 9.83 (s, 1H), 8.49 (d, J=8.3 Hz, 1H), 8.45 (s, 1H), 7.87 (t, J=7.8 Hz, 1H), 7.74 (s, 1H), 7.68 (d, J=7.2 Hz, 1H), 7.62-7.50 (m, 2H), 7.39 (s, 1H), 7.32-7.21 (m, 1H), 5.25 (s, 2H), 5.19 (dd, J=12.8, 5.3 Hz, 1H), 5.16 (s, 2H), 4.71 (t, J=6.5 Hz, 2H), 4.24 (s, 3H), 3.02-2.87 (m, 2H), 2.69-2.50 (m, 4H), 2.23-2.11 (m, 2H), 1.91-1.83 (m, 2H), 1.72-1.65 (m, 2H).

$^{13}$C NMR (101 MHz, DMSO) δ 173.19, 172.09, 170.32, 168.12, 167.10, 155.63, 155.22, 150.49, 150.43, 148.55, 146.67, 146.39, 146.02, 143.79, 136.88, 136.52, 132.38, 132.01, 129.14, 127.38, 126.96, 125.95, 120.78, 120.55, 118.88, 117.66, 116.74, 116.42, 106.14, 50.02, 40.39, 40.16, 38.24, 35.92, 35.27, 32.32, 31.589, 25.2.

Example 11

Compound 11: (E)-7-(4-((4-(((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-dioxopiperidin-3-yl)-1,3-dioxoisoindolin-4-yl)heptamide

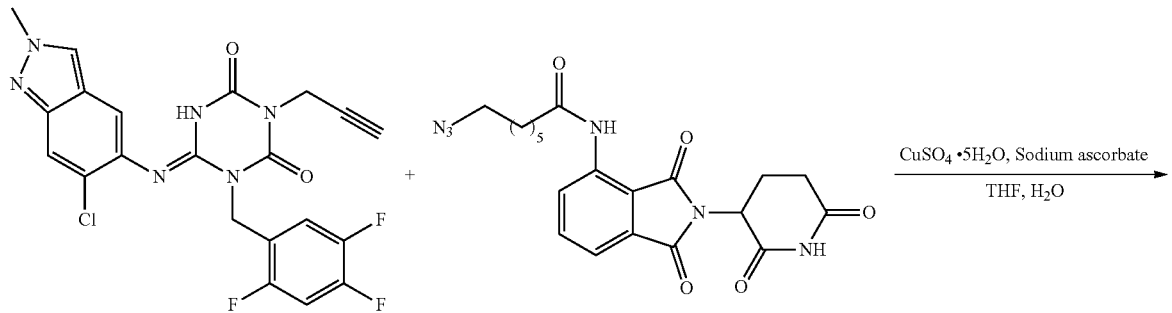

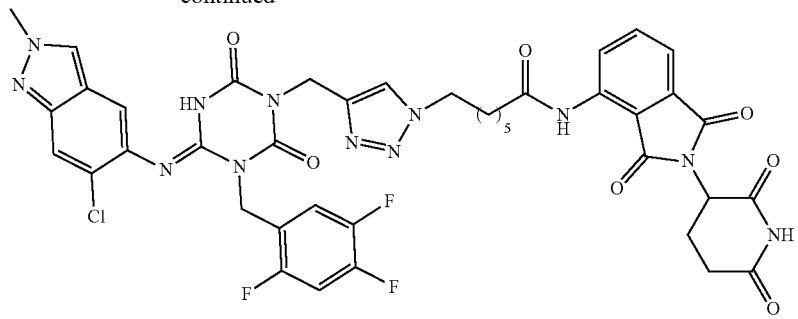

Compound 11 was prepared in the same way as Compound 1 with different starting materials, a yield of 19.53%.

$^1$H NMR (400 MHz, DMSO) δ 11.13 (s, 1H), 9.88 (s, 1H), 9.82 (s, 1H), 8.44 (d, J=8.3 Hz, 1H), 8.41 (s, 1H), 7.83 (t, J=7.8 Hz, 1H), 7.75 (s, 1H), 7.69 (d, J=7.2 Hz, 1H), 7.61-7.52 (m, 2H), 7.36 (s, 1H), 7.31-7.20 (m, 1H), 5.27 (s, 2H), 5.21 (dd, J=12.8, 5.3 Hz, 1H), 5.18 (s, 2H), 4.74 (t, J=6.5 Hz, 2H), 4.22 (s, 3H)), 3.04-2.85 (m, 2H), 2.72-2.55 (m, 4H), 2.24-1.88 (m, 6H), 1.82-1.68 (m, 2H).

$^{13}$C NMR (101 MHz, DMSO) δ 173.20, 172.12, 170.34, 168.16, 167.12, 155.67, 155.34, 150.83, 150.52, 148.67, 146.80, 146.42, 146.12, 143.80, 136.81, 136.12, 132.42, 132.10, 129.21, 127.42, 126.93, 125.91, 120.92, 120.51, 118.82, 117.76, 116.77, 116.38, 106.16, 50.09, 40.42, 40.18, 35.88, 32.43, 31.54, 27.34, 23.92, 22.45.

Example 12

Compound 12: (E)-8-(4-((4-(((6-Chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)-N-(2-Preparation of (2,6-dioxopiperidin-3-yl)-1,3-dioxoisoindolin-4-yl)octamide Compound 12 was prepared in the same way as Compound 1 with different starting materials, a yield of 15.87%.

$^1$H NMR (400 MHz, DMSO) δ 11.09 (s, 1H), 9.91 (s, 1H), 9.79 (s, 1H), 8.46 (d, J=8.3 Hz, 1H), 8.39 (s, 1H), 7.87 (t, J=7.8 Hz, 1H), 7.79 (s, 1H), 7.71 (d, J=7.2 Hz, 1H), 7.64-7.50 (m, 2H), 7.39 (s, 1H), 7.32-7.23 (m, 1H), 5.31 (s, 2H), 5.24 (dd, J=12.8, 5.3 Hz, 1H), 5.21 (s, 2H), 4.78 (t, J=6.5 Hz, 2H), 4.25 (s, 3H), 3.01-2.82 (m, 2H), 2.68-2.35 (m, 4H), 2.14-1.82 (m, 6H), 1.74-1.54 (m, 4H).

$^{13}$C NMR (101 MHz, DMSO) δ 173.22, 172.15, 170.42, 168.23, 167.17, 155.71, 155.39, 150.97, 150.58, 148.71, 146.89, 146.56, 146.09, 143.85, 136.79, 136.09, 132.45, 132.14, 129.19, 127.45, 126.88, 125.89, 120.89, 120.49, 118.79, 117.81, 116.79, 116.41, 106.21, 50.11, 40.52, 40.21, 38.41, 35.32, 32.63, 31.44, 27.34, 25.56, 22.92, 21.65.

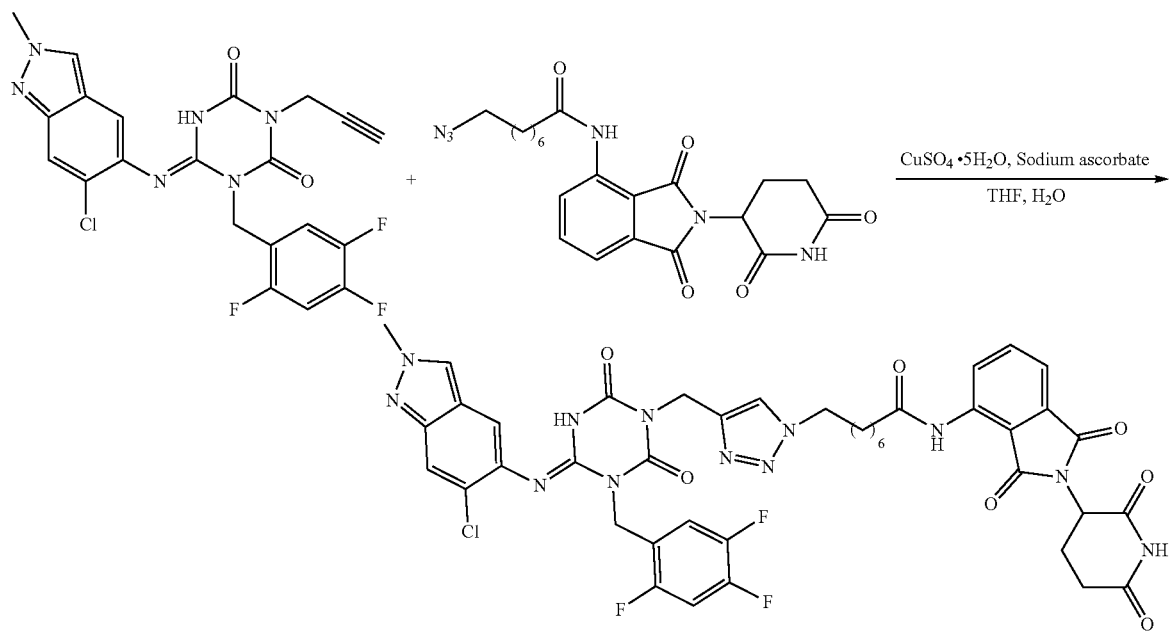

Example 13

Compound 13: (E)-2-(2-(4-((4-((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)ethoxy yl)-N-(2-(2,6-dioxopiperidin-3-yl)-1-oxoisoquinolin-4-yl)acetamide (1) Preparation of Compound (a4)

The preparation method was the same as in Example 1.

(2) Preparation of Compound (d1)

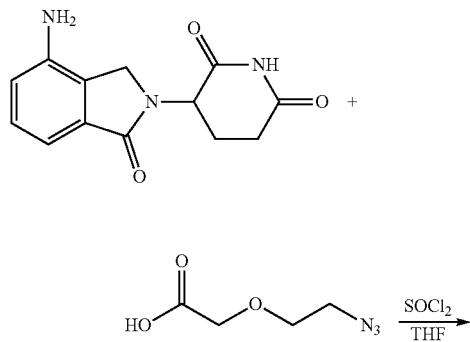

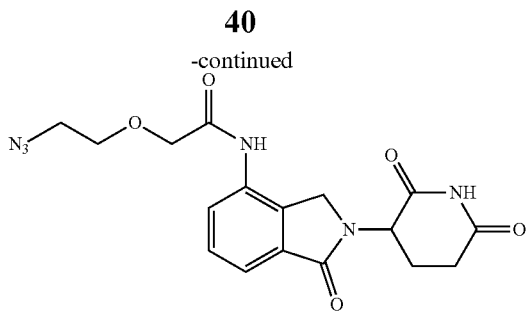

d1

2-(2-Azidoethoxy)acetic acid (290.2 mg, 2 mmol) was dissolved in 5 mL of thionyl chloride, and heated to reflux for 2 hours. After the reaction was complete, the reaction mixture was concentrated under reduced pressure to remove the solvent, and lenalidomide (1 mmol, 259.3 mg) was then added, with 10 mL of tetrahydrofuran used as a solvent. The reaction was heated under reflux for 5 hours, and monitored by TLC. After the reaction was completed, the reaction mixture was cooled to room temperature, 2 mL of methanol was added, and the mixture was continued to stir for 1 hour. The solvent was removed by concentration under reduced pressure, and 296.8 mg of compound (d1) was obtained by column chromatography (eluent: dichloromethane:methanol (V:V)=10:1), a yield of 76.83%.

(3) Preparation of Compound 13

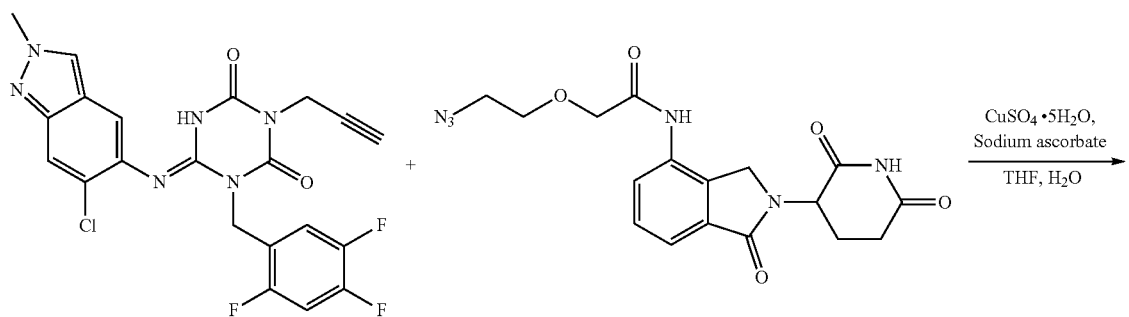

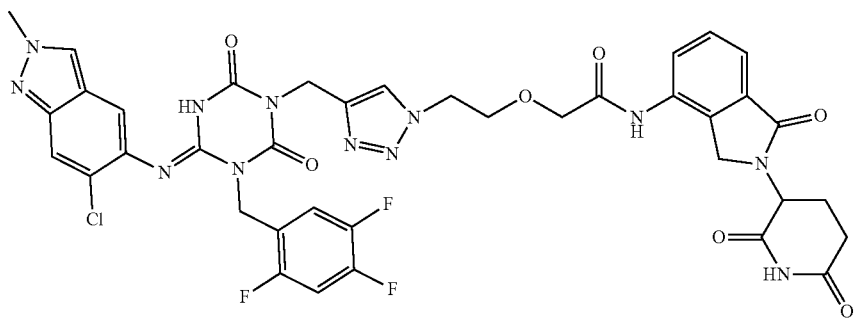

Compound (a4) (142.4 mg, 0.3 mmol), compound (d1) (139.1 mg, 0.36 mmol), copper sulfate pentahydrate (30.0 mg, 0.12 mmol), and sodium ascorbate (23.8 mg, 0.12 mmol) were placed in a reactor, and dissolved in a mixture of 10 mL tetrahydrofuran and 1 mL water. The mixture was heated and stirred at 45° C. under argon overnight, and monitored by TLC. After the reaction was complete, the reaction mixture was concentrated under reduced pressure to remove the solvent, separated and purified by column chromatography (eluent: dichloromethane:methanol (V:V)=20: 1), and dried to obtain 66.2 mg of compound 13, a yield of 25.63%.

$^1$H NMR (400 MHz, DMSO) δ 11.12 (s, 1H), 9.83 (s, 1H), 9.30 (s, 1H), 8.42 (s, 1H), 7.95 (d, J=7.1 Hz, 1H), 7.75 (s, 1H), 7.65-7.53 (m, 2H), 7.46-7.35 (m, 2H), 7.31 (s, 1H), 7.26-7.13 (m, 1H), 5.247) (dd, J=13.3, 4.8 Hz, 1H), 5.04 (s, 2H), 4.58 (s, 2H), 4.31 (s, 2H), 4.12 (3H, s), 3.95-3.82 (m, 2H), 3.75 (t, J=7.1 Hz, 2H), 2.80-2.65 (m, 2H), 2.43-2.24 (m, 2H).

$^{13}$C NMR (101 MHz, DMSO) δ 173.52, 171.32, 171.12, 168.42, 155.69, 155.31, 150.56, 150.48, 148.60, 146.61, 146.34, 145.70, 143.89, 134.38, 133.11, 132.21, 129.14, 129.06, 127.28, 125.92, 125.73, 120.69, 120.38, 119.46, 118.09, 116.81, 116.36, 106.09, 69.10, 68.24, 52.08, 51.73, 46.92, 40.31, 40.10, 38.07, 31.55, 29.18.

Example 14

Compound 14: (E)-2-(2-(2-(4-((4-((6-chloro-2-methyl-2H-indazol-5-yl)imino)-2,6-Dioxy-3-(2,4,5-trifluorobenzyl)-1,3,5-triazin-1-yl)methyl)-1H-1,2,3-triazol-1-yl)ethoxy)ethoxy)-N-(2-(2,6-dioxopiperidin-3-yl)-1-oxoisoindolin-4-yl)acetamide

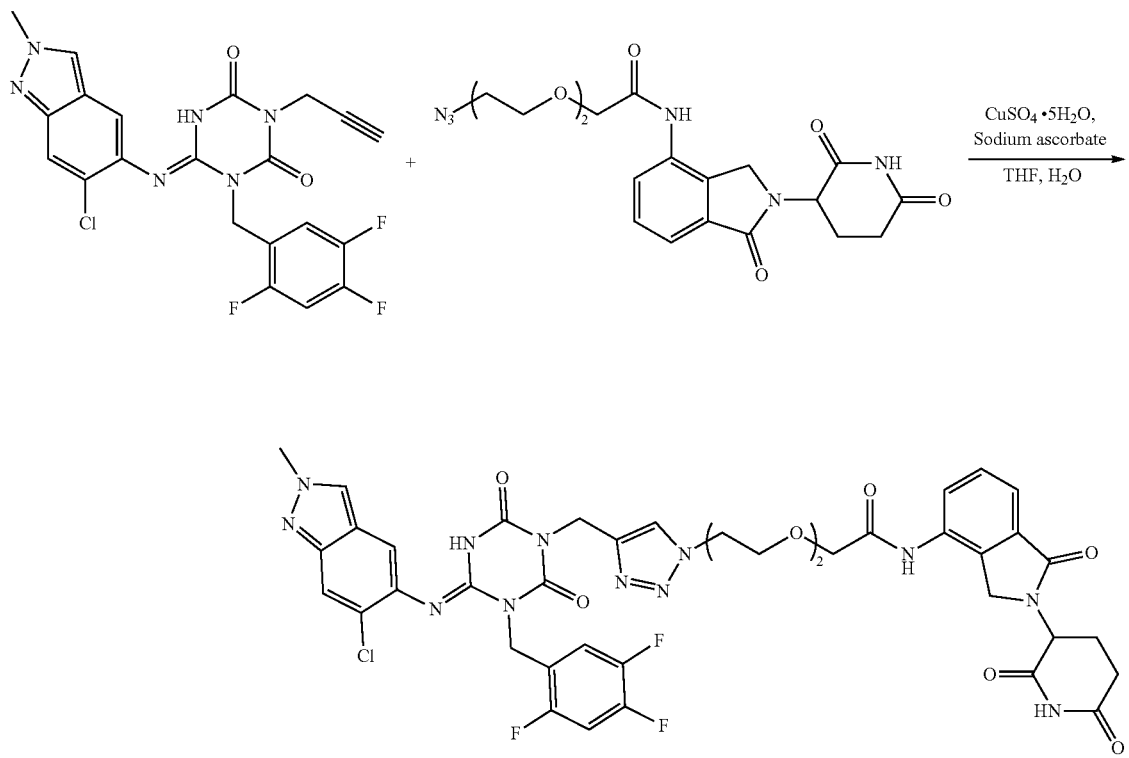

Compound 14 was prepared in the same way as Compound 13 with different starting materials, a yield of 21.45%.

$^1$H NMR (400 MHz, DMSO) δ 11.23 (s, 1H), 9.86 (s, 1H), 9.33 (s, 1H), 8.38 (s, 1H), 7.89 (d, J=7.1 Hz, 1H), 7.73 (s, 1H), 7.60-7.51 (m, 2H), 7.41-7.32 (m, 2H), 7.28 (s, 1H), 7.22-7.14 (m, 1H), 5.22 (s, 2H), 5.16 (dd, J=13.3, 4.8 Hz, 1H), 5.01 (s, 2H), 4.49 (s, 2H), 4.28 (s, 2H), 4.09 (3H, s), 3.85-3.74 (m, 2H), 3.64 (t, J=7.1 Hz, 2H), 3.35 (s, 4H), 2.76-2.59 (m, 2H), 2.23-2.04 (m, 2H).

$^{13}$C NMR (101 MHz, DMSO) δ 173.68, 171.42, 171.23, 168.38, 155.71, 155.34, 150.61, 150.52, 148.63, 146.66, 146.31, 145.72, 143.91, 134.42, 133.12, 132.24, 129.16, 129.01, 127.32, 125.91, 125.77, 120.71, 120.42, 119.51, 118.11, 116.84, 116.32, 106.14, 69.16, 68.45, 68.34, 68.16, 52.12, 51.75, 46.96, 40.34, 313.06, 298.1.

Example 15

Compound 15: (E)-2-(2-(2-(2-(4-((4-((6-chloro-2-methyl-2H-indazol-5-yl)imino)-2,6-Dioxy-3-(2,4,5-trifluorobenzyl)-1,3,5-triazin-1-yl)methyl)-1H-1,2,3-triazole-1-yl)ethoxy)ethoxy)ethoxy)-N-(2-(2,6-dioxopiperidin-3-yl)-1-oxoisoindolin-4-yl)ethyl Preparation of amides

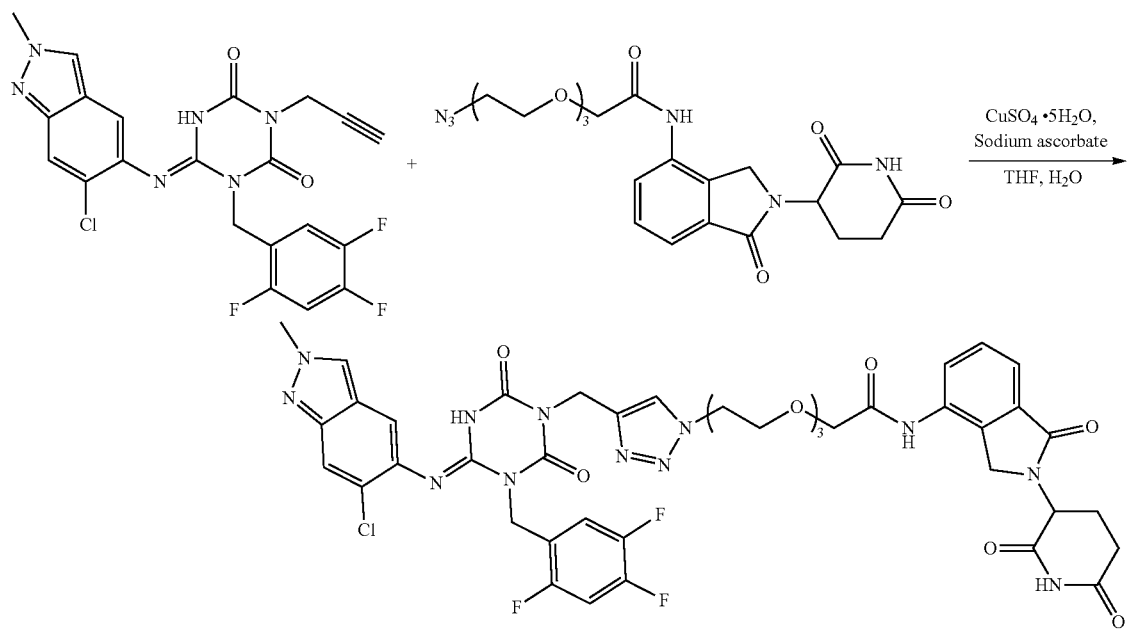

Compound 15 was prepared in the same way as Compound 13 with different starting materials, a yield of 16.36%.

$^1$H NMR (400 MHz, DMSO) δ 11.18 (s, 1H), 9.82 (s, 1H), 9.41 (s, 1H), 8.43 (s, 1H), 7.92 (d, J=7.1 Hz, 1H), 7.71 (s, 1H), 7.65-7.54 (m, 2H), 7.44-7.33 (m, 2H), 7.29 (s, 1H), 7.24-7.16 (m, 1H), 5.19 (s, 2H), 5.12 (dd, J=13.3, 4.8 Hz, 1H), 5.03 (s, 2H), 4.51 (s, 2H), 4.32 (s, 2H), 4.08 (3H, s), 3.82-3.71 (m, 2H), 3.63 (t, J=7.1 Hz, 2H), 3.39 (s, 8H), 2.67-2.53 (m, 2H), 2.24-2.07 (m, 2H).

$^{13}$C NMR (101 MHz, DMSO) δ 173.71, 171.46, 171.25, 168.42, 155.78, 155.41, 150.69, 150.58, 148.67, 146.72, 146.35, 145.71, 144.02, 134.46, 133.21, 132.25, 129.22, 129.08, 127.34, 126.02, 125.81, 120.77, 120.45, 119.53, 118.17, 116.84, 116.36, 106.16, 70.41, 70.12, 69.21, 68.46, 68.21, 52.82, 47.03, 40.19, 31.62, 29.27, 29.27.

Example 16

Compound 16: (E)-2-(2-(4-((4-((6-chloro-2-methyl-2H-indazol-5-yl)imino)-2,6-dioxy-3-(2,4,5-Trifluorobenzyl)-1,3,5-triazin-1-yl)methyl)-1H-1,2,3-triazol-1-yl)ethoxy yl)-N-(2-(2,6-dioxopiperidin-3-yl)-1,3-dioxoisoindolin-4-yl)acetamide

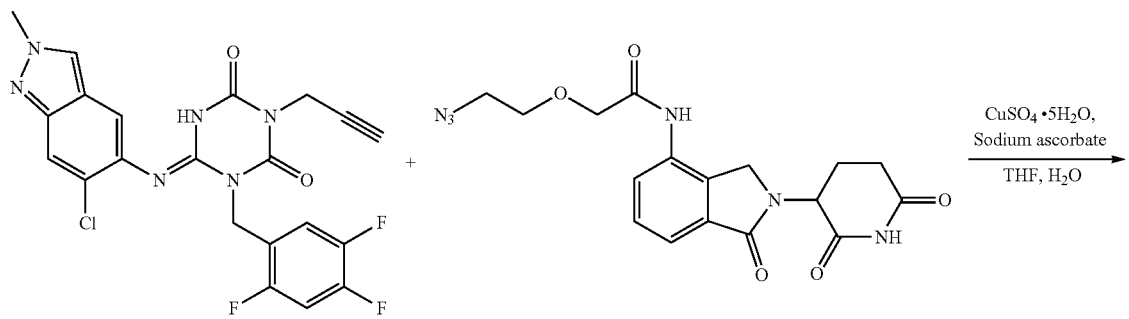

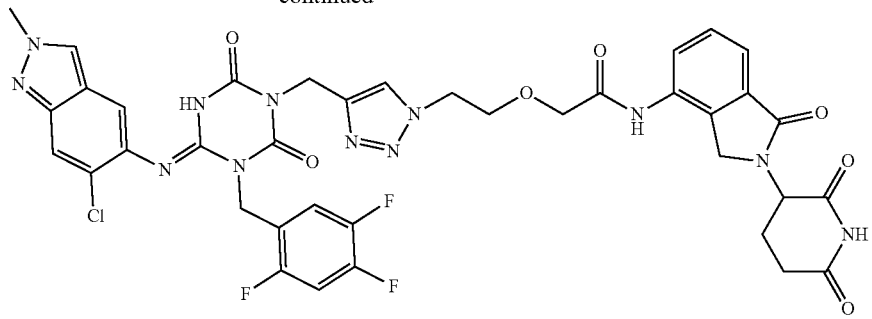

Compound 16 was prepared in the same way as Compound 13 with different starting materials, a yield of 26.44%.

¹H NMR (400 MHz, DMSO) δ 11.11 (s, 1H), 9.82 (s, 1H), 9.75 (s, 1H), 8.44 (d, J=8.3 Hz, 1H), 8.36 (s, 1H), 7.81 (t, J=7.8 Hz, 1H), 7.72 (s, 1H), 7.65 (d, J=7.2 Hz, 1H), 7.60-7.51 (m, 2H), 7.43 (s, 1H), 7.31-7.19 (m, 1H), 5.26 (s, 2H), 5.12 (dd, J=12.8, 5.3 Hz, 1H), 5.16 (s, 2H), 4.48 (s, 2H), 4.19 (s, 3H), 3.73-3.58 (m, 2H), 3.51 (t, J=6.8 Hz, 2H), 2.32-2.19 (m, 2H), 2.10-1.93 (m, 2H).

¹³C NMR (101 MHz, DMSO) δ 173.42, 172.31, 170.48, 168.19, 167.26, 155.82, 155.34, 150.91, 150.58, 148.66, 146.71, 146.38, 145.92, 143.79, 136.89, 136.67, 132.34, 131.91, 129.48, 127.29, 126.91, 125.95, 120.81, 120.47, 118.90, 117.83, 116.71, 116.42, 106.25, 68.91, 67.23, 52.14, 48.37, 40.41, 39.92, 37.06, 32.32, 28.

Compound 17 was prepared in the same way as Compound 13 with different starting materials, a yield of 20.81%.

¹H NMR (400 MHz, DMSO) δ 11.16 (s, 1H), 9.79 (s, 1H), 9.70 (s, 1H), 8.41 (d, J=8.3 Hz, 1H), 8.33 (s, 1H), 7.82 (t, J=7.8 Hz, 1H), 7.71 (s, 1H), 7.63 (d, J=7.2 Hz, 1H), 7.59-7.47 (m, 2H), 7.42 (s, 1H), 7.32-7.21 (m, 1H), 5.28 (s, 2H), 5.14 (dd, J=12.8, 5.3 Hz, 1H), 5.19 (s, 2H), 4.52 (s, 2H), 4.21 (s, 3H), 3.76-3.61 (m, 2H), 3.48 (t, J=6.8 Hz, 2H), 3.39 (s, 4H), 2.28-2.17 (m, 2H), 2.11-1.95 (m, 2H).

¹³C NMR (101 MHz, DMSO) δ 173.38, 172.28, 170.51, 168.21, 167.22, 155.84, 155.36, 150.89, 150.62, 148.65, 146.73, 146.42, 145.91, 143.80, 136.94, 136.72, 132.36, 131.88, 129.54, 127.34, 126.85, 125.88, 120.79, 120.52, 118.93, 117.80, 116.74, 116.42, 106.21, 69.74, 69.12, 68.85, 17.22, 52.16, 48.39, 40.38, 39.91, 27.4.

Example 17

Compound 17: (E)-2-(2-(2-(4-((4-((6-chloro-2-methyl-2H-indazol-5-yl)imino)-2,6-Dioxy-3-(2,4,5-trifluorobenzyl)-1,3,5-triazin-1-yl)methyl)-1H-1,2,3-triazol-1-yl)ethoxy)ethoxy)-N-(2-(2,6-dioxopiperidin-3-yl)-1,3-dioxoisoquinolin-4-yl) acetamide Example 18

Compound 18. (E)-2-(2-(2-(2-(4-((4-((6-chloro-2-methyl-2H-indazol-5-yl)imino)-2,6-Dioxy-3-(2,4,5-trifluorobenzyl)-1,3,5-triazin-1-yl)methyl)-1H-1,2,3-triazole-1-yl)ethoxy)ethoxy)ethoxy)-N-(2-(2,6-dioxopiperidin-3-yl)-1,3-dioxoisoquinolin-4-yl) Preparation of acetamide

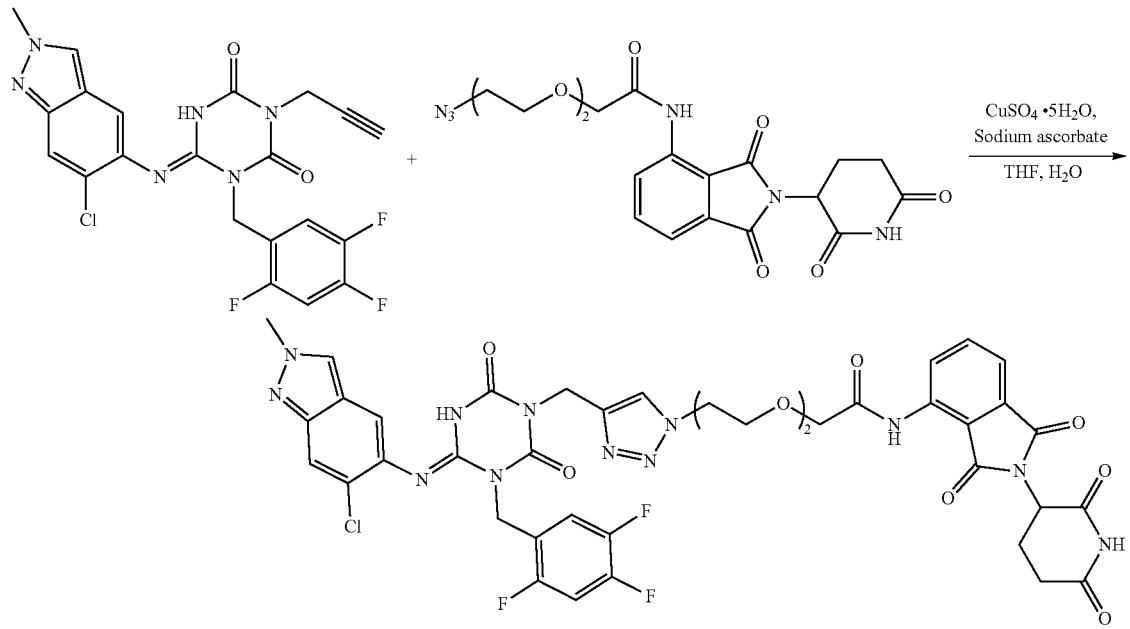

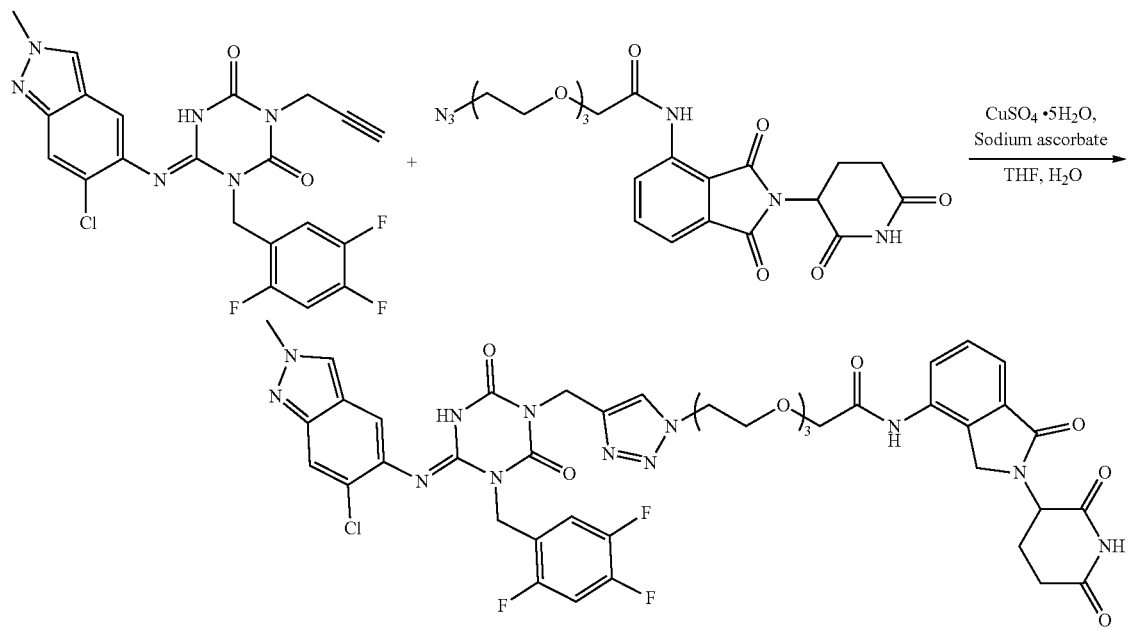

Compound 18 was prepared in the same way as Compound 13 with different starting materials, a yield of 17.26%.

$^1$H NMR (400 MHz, DMSO) δ 11.15 (s, 1H), 9.82 (s, 1H), 9.75 (s, 1H), 8.47 (d, J=8.3 Hz, 1H), 8.37 (s, 1H), 7.84 (t, J=7.8 Hz, 1H), 7.73 (s, 1H), 7.65 (d, J=7.2 Hz, 1H), 7.60-7.49 (m, 2H), 7.42 (s, 1H), 7.34-7.20 (m, 1H), 5.33 (s, 2H), 5.16 (dd, J=12.8, 5.3 Hz, 1H), 5.21 (s, 2H), 4.49 (s, 2H), 4.18 (s, 3H), 3.73-3.59 (m, 2H), 3.53 (t, J=6.8 Hz, 2H), 3.42 (s, 8H), 2.23-2.14 (m, 2H), 2.06-1.87 (m, 2H).

$^{13}$C NMR (101 MHz, DMSO) δ 173.42, 172.33, 170.49, 168.28, 167.23, 155.92, 155.34, 150.90, 150.63, 148.67, 146.76, 146.44, 145.96, 143.83, 136.92, 136.71, 132.38, 131.90, 129.51, 127.36, 126.87, 125.91, 120.83, 120.54, 118.91, 117.87, 116.72, 116.48, 106.25, 71.01, 70.87, 69.68, 68.90, 67.43, 52.25, 40.52, 39.98, 32.27, 28.96.

2. Bioactivity Assay (1) 3CL$^{pro}$ Inhibitory Activity Test

The inhibitory activity of the compounds against SARS-CoV-2 3CL$^{pro}$ was determined using fluorescence resonance energy transfer.

10 μL of the compound solutions prepared at different concentrations (final concentrations of 1000, 500, 250, 125, 62.5, 31.25, 15.63, 7.81, 3.90, 1.95 nM, in DMSO) and 40 L of SARS-CoV-2 3CL$^{pro}$ (Shanghai Biyuntian Biotechnology Co., Ltd., final concentration: 0.5 μM, diluted with Tris-HCl buffer (20 mM Tris-HCl, 100 mM NaCl, 1 mM EDTA, pH 7.4)) were mixed, added to a black 96-well plate, incubate at 37° C. for 10 min. A reaction was initiated by adding 50 μL of the fluorescent substrate Dabcyl-KT-SAVLQSGFRKME-Edans (Shanghai Biyuntian Biotechnology Co., Ltd., the final concentration: 20 μM), incubated for 10 min, and measured by a multifunctional microplate reader (Thermo Fisher Scientific Co., Ltd., Varioskan Flash) for fluorescence detection, the excitation wavelength: 340 nm, the emission wavelength: 490 nm. The fluorescence value was recorded to calculate the inhibition percentage of the sample. DMSO without compound was used as the enzyme activity control, and the Tris-HCl buffer without SARS-CoV-2 3CL$^{pro}$ was used as the blank control, and the treatment methods were the same. The IC$_{50}$ values of the samples (compounds 1-18) were calculated by nonlinear regression analysis using GraphPad Prism software.

Inhibition Rate (%)=(RFU$_{enzyme\ activity\ control}$−
RFU$_{sample}$)/(RFU$_{enzyme\ activity\ control}$−
RFU$_{blank\ control}$)×100%

The experimental results are shown in Table 1 (in Table 1, the column of IC$_{50}$, A: IC50<100 nM, B: IC$_{50}$=100-1000 nM), the example compounds all have inhibitory activity against 3CL$^{pro}$, among which compounds 3, 4, 8, 9, 10, 14 and 17 have strong inhibitory effects on 3CL$^{pro}$, with IC$_{50}$ values below 100 nM.

(2) Determination of 3CL$^{pro}$ Degradation Activity by Western Blot

HEK293E cells in logarithmic growth phase (the Cell Bank of the Chinese Academy of Sciences) were seeded in a 6-well plate at a density of 6.0×105 cells/well, and incubated in a 37° C. incubator with 5% CO2 for 8-24 h. When the density reached 70% confluence, the plate was replaced with 2 mL of pre-warmed serum-free medium (Shanghai Opmax Biotechnology Co., Ltd.). The SARS-CoV-2 3CL$^{pro}$ expression plasmid (2 μg/well, prepared in 1×HBS, Beijing Yiqiao Shenzhou Technology Co., Ltd.) was transfected with 10 μM PEI (polyethyleneimine, Shanghai McLean Biochemical Technology Co., Ltd.) at a mass-to-volume ratio of 3:4. The PEI-plasmid mixture was added dropwise to the above serum-free medium, gently shaken mixed, and incubated in a 37° C. incubator containing 5% CO$_2$ for 10 h. The medium containing transfection reagent was removed and medium containing gradient concentrations of the samples to be tested (final sample concentrations of 1000, 500, 250, 125, 62.5, 31.25, 15.63, 7.81, 3.90, 1.95 nM) was added. After culturing at 37° C. and 5% CO$_2$ for 24 h, the supernatant was discarded, the cells were collected, and RIPA cell lysis buffer (Shanghai McLean Biochemical Technology Co., Ltd.) was added to lyse the cells on ice for 30 min, and the expression of 3CL$^{pro}$ was detected by Western Blot. Image J analyzed the relative expression of 3CL$^{pro}$ and calculated the protein degradation rate. The medium without the sample to be tested was used as the control group, and the rest of the treatment methods were the same. The protein degradation activity ($DC_{50}$) of the samples was calculated by nonlinear regression analysis using GraphPad Prism software.

Degradation rate (%)=($3CL^{pro}$ relative expression$_{control\ group}$−$3CL^{pro}$ relative$_{sample\ group}$)/$3CL^{pro}$ relative$_{control\ group}$×100%

The experimental results are shown in Table 1 (in Table 1, $DC_{50}$ is in the column, A: $DC_{50}$<100 nM, B: $DC_{50}$=100-1000 nM), the example compounds all have degrading activity on 3CLpro, among which compounds 2, 3, 4, 5, 8, 9, 10, 13, 14, 15, 16 and 17 had stronger degradation activities against $3CL^{pro}$, and the $DC_{50}$ values were all below 100 nM.

TABLE 1

Inhibitory activity and degradation activity of compounds 1-18 on $3CL^{pro}$

| Compounds | $IC_{50}$ (nM) | $DC_{50}$ (nM) |
|---|---|---|
| 1 | B | B |
| 2 | B | A |
| 3 | A | A |
| 4 | A | A |
| 5 | B | A |
| 6 | B | B |
| 7 | B | B |
| 8 | A | A |
| 9 | A | A |
| 10 | A | A |
| 11 | B | B |
| 12 | B | B |
| 13 | B | A |
| 14 | A | A |
| 15 | B | A |
| 16 | B | A |
| 17 | A | A |
| 18 | B | B |

The data in Table 1 shows that compounds 1-18 have different degrees of inhibition and degradation of $3CL^{pro}$. The $IC_{50}$ and $DC_{50}$ values of compounds 3, 4, 8, 9, 10, 14 and 17 against $3CL^{pro}$ are all less than 100 nM. It also shows that the compounds of the present invention have both inhibitory activity and good degradation activity on $3CL^{pro}$, and can be developed and studied as anti-coronavirus candidate drugs.

The above content is only to illustrate the technical idea of the present invention, and cannot limit the protection scope of the present invention. Any modification made on the basis of the technical solution proposed in accordance with the technical idea of the present invention falls within the scope of the claims of the present invention.

The invention claimed is:

1. A compound of formula I or formula II, a pharmaceutically acceptable salt, or a tautomer thereof:

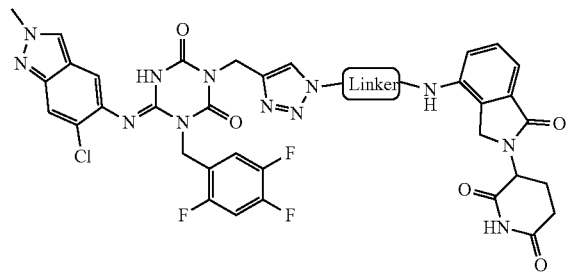

formula I or

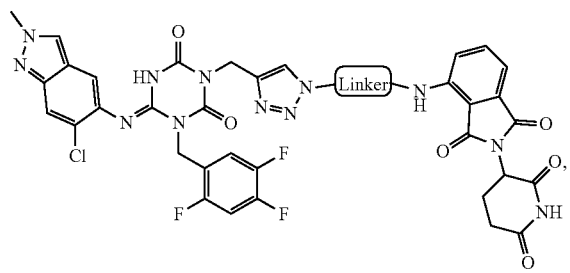

formula II wherein, the Linker is

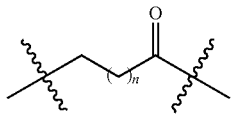

or

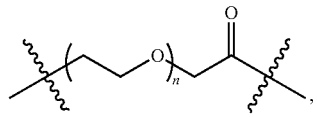

n and n is 1-6.

2. The compound of claim 1, wherein the compound is selected from the group consisting of:

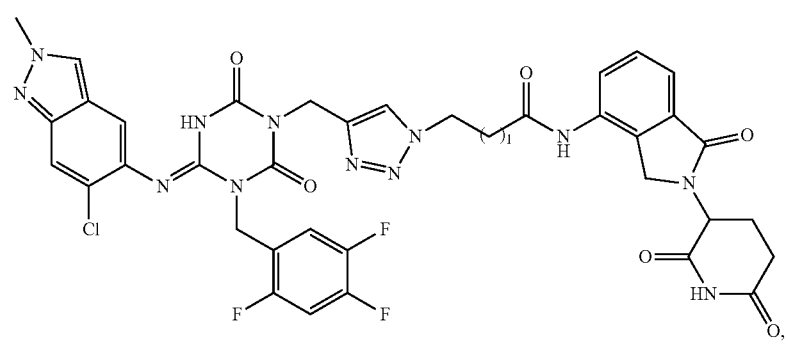

1

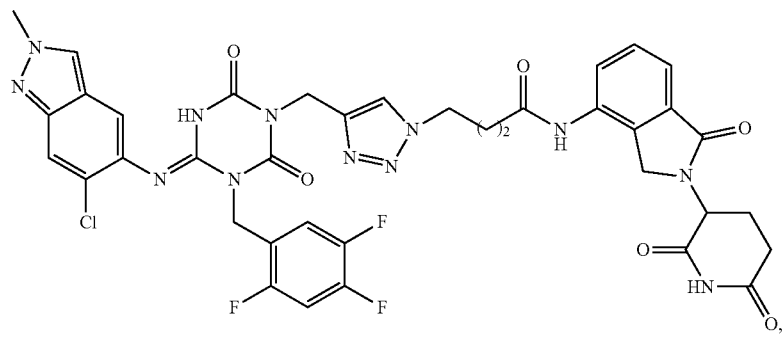
2
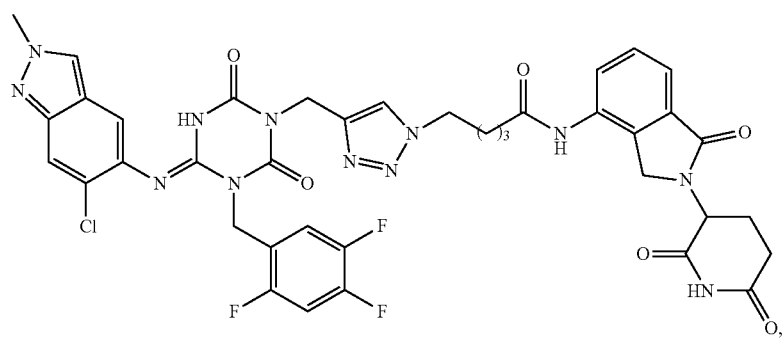
3
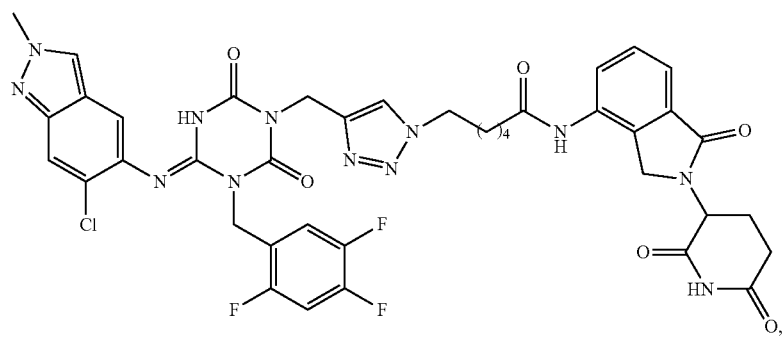
4
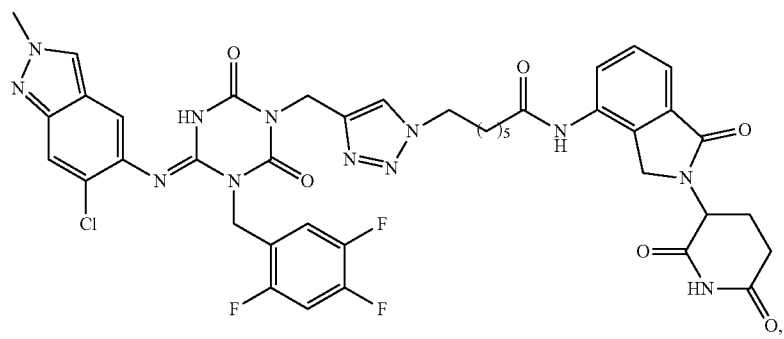
5

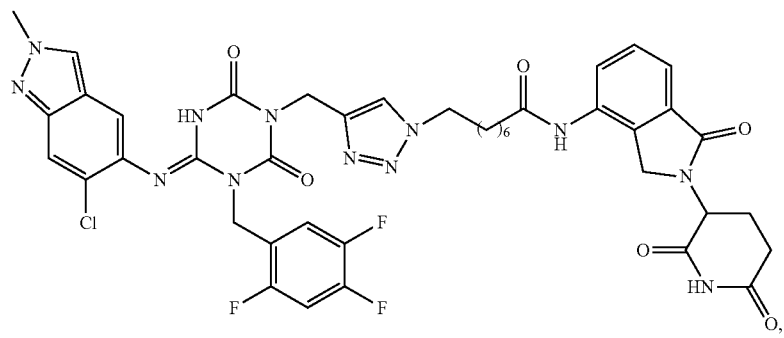
6
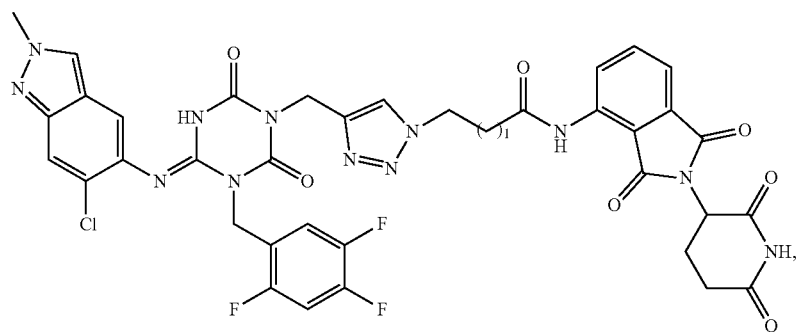
7
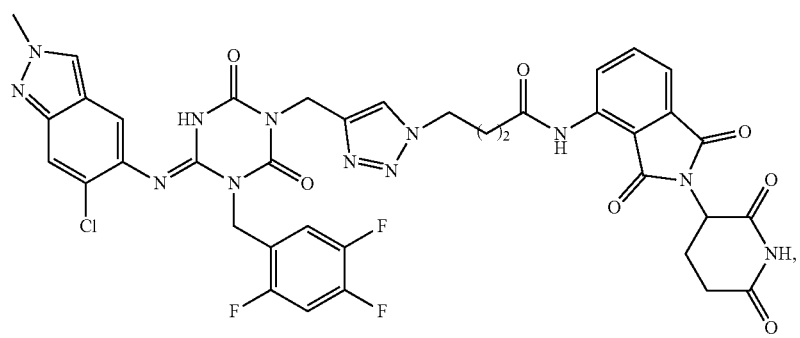
8
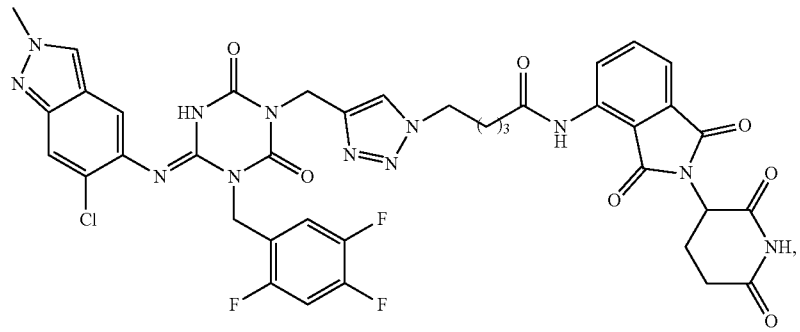
9

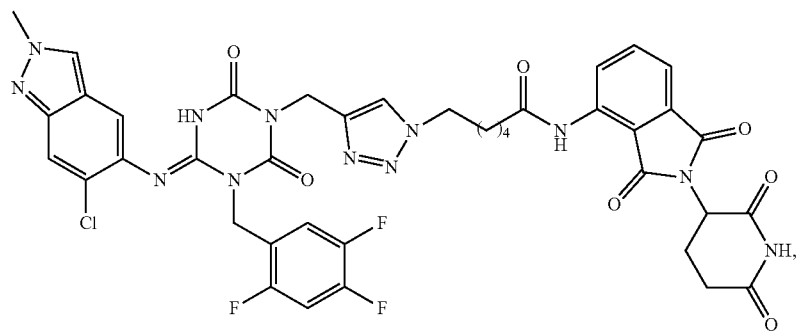
10
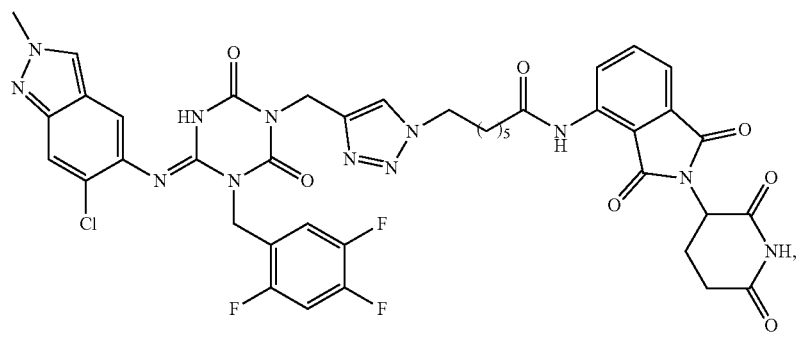
11
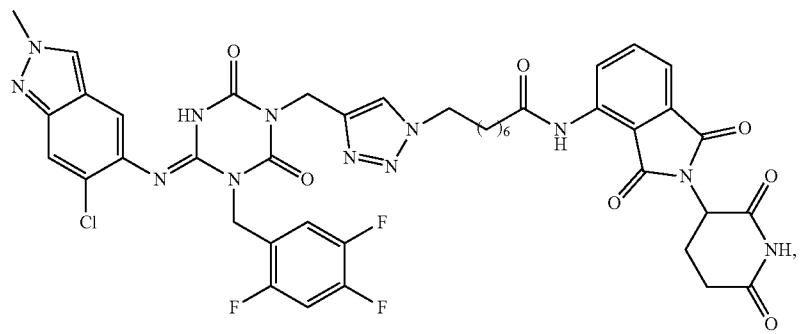
12
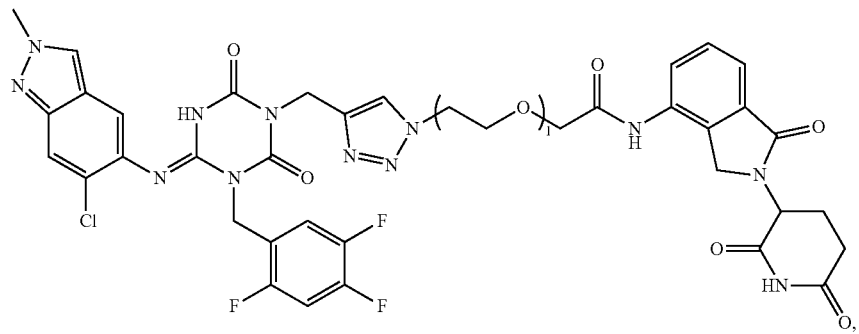
13

14
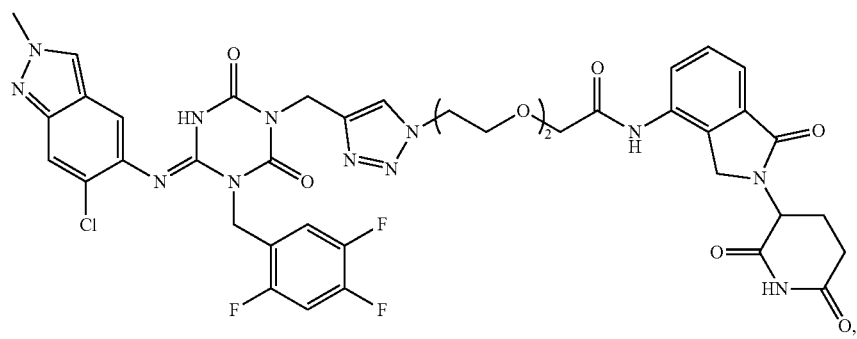
15
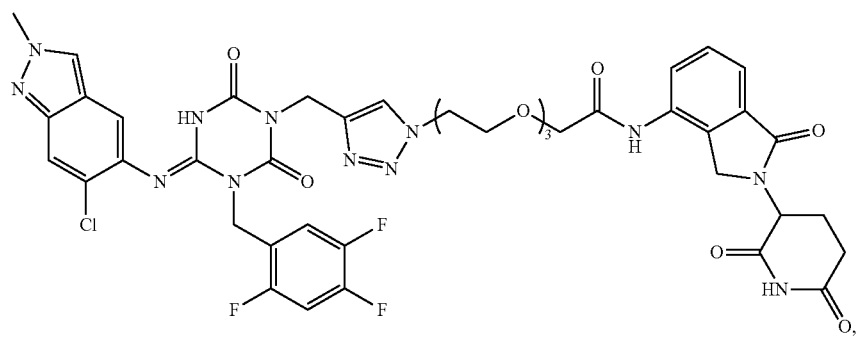
16
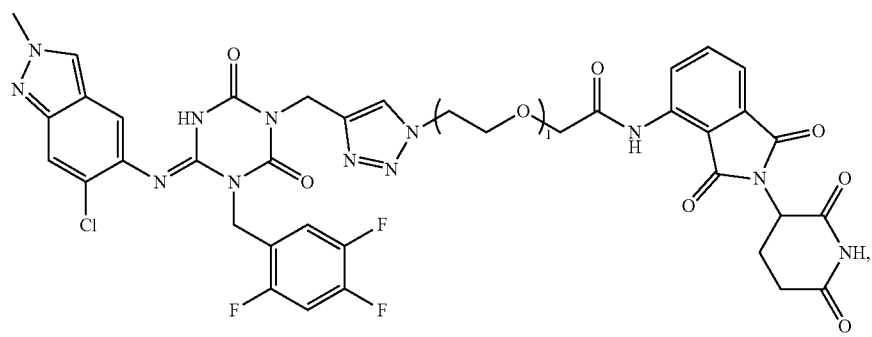
17
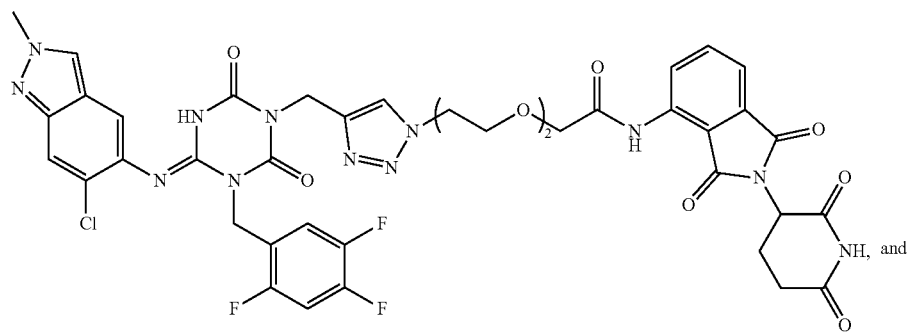

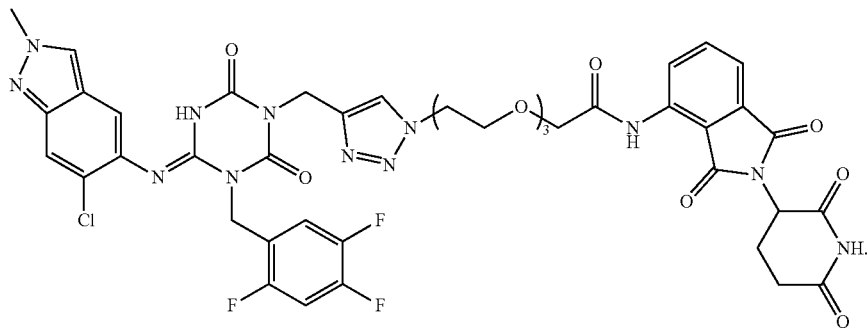

18

3. The compound of claim 1, wherein the pharmaceutically acceptable salt comprises one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid, and aspartic acid.

4. An anti-coronavirus pharmaceutical preparation comprising the compound of claim 1.

5. The anti-coronavirus pharmaceutical preparation of claim 4, wherein the coronavirus is novel coronavirus SARS-CoV-2.

* * * * *